US011006909B2

(12) United States Patent
Yifat et al.

(10) Patent No.: US 11,006,909 B2
(45) Date of Patent: May 18, 2021

(54) RADIATION SHIELDING APPARATUSES AND APPLICATIONS THEREOF

(71) Applicant: Radiaction Ltd., Tel Aviv (IL)

(72) Inventors: Jonathan Yifat, Ramat Hasharon (IL); Amir Belson, Savyon (IL); Amichay Gross, Herzliya (IL)

(73) Assignee: Radiaction, Ltd.

( * ) Notice: Subject to any disclaimer, the term of this patent is extended or adjusted under 35 U.S.C. 154(b) by 178 days.

(21) Appl. No.: 15/972,051

(22) Filed: May 4, 2018

(65) Prior Publication Data
US 2018/0249972 A1    Sep. 6, 2018

Related U.S. Application Data

(63) Continuation of application No. PCT/US2016/061202, filed on Nov. 9, 2016.
(Continued)

(51) Int. Cl.
*H01J 35/16* (2006.01)
*A61B 6/10* (2006.01)
(Continued)

(52) U.S. Cl.
CPC ............ *A61B 6/107* (2013.01); *A61B 6/4441* (2013.01); *A61N 5/1081* (2013.01); *G01T 1/00* (2013.01);
(Continued)

(58) Field of Classification Search
CPC ....... A61B 6/102; A61B 6/107; A61B 6/4441; A61B 6/547; A61B 6/4423; A61B 6/487;
(Continued)

(56) References Cited

U.S. PATENT DOCUMENTS

| 4,062,518 | A | * | 12/1977 | Stivender | ................ A61B 6/04 |
| | | | | | 250/519.1 |
| 4,581,538 | A | * | 4/1986 | Lenhart | .................... G21F 3/00 |
| | | | | | 250/515.1 |

(Continued)

FOREIGN PATENT DOCUMENTS

| CN | 202665566 U | 1/2013 |
| KR | 101218378 B1 | 1/2013 |
| WO | WO-2017083437 A1 | 5/2017 |

OTHER PUBLICATIONS

EESR for EP16864950.7 dated May 29, 2019.

*Primary Examiner* — Irakli Kiknadze
(74) *Attorney, Agent, or Firm* — Wilson Sonsini Goodrich & Rosati

(57) ABSTRACT

Apparatuses (devices, systems) and methods for shielding (protecting) surroundings around periphery of regions of interest located inside objects (e.g., patients) from radiation emitted by X-ray systems towards the objects. Apparatus includes: at least one radiation shield assembly including a support base connectable to an X-ray system radiation source or detector, and a plurality of radiation shield segments sequentially positioned relative to the support base, thereby forming a contiguous radiopaque screen configured for spanning around the region of interest periphery with a radiopaque screen edge opposing the object. Radiation shield segments are individually, actively controllable to extend or contract to selected lengths with respective free ends in directions away from or towards the support base(s), for locally changing contour of the radiopaque screen edge. Applicable for shielding (protecting) medical personnel, and patients, from exposure to X-ray radiation during medical interventions or/and diagnostics.

32 Claims, 23 Drawing Sheets

Related U.S. Application Data

(60) Provisional application No. 62/252,664, filed on Nov. 9, 2015, provisional application No. 62/354,932, filed on Jun. 27, 2016.

(51) Int. Cl.
  *G21F 3/00*   (2006.01)
  *G01T 1/04*   (2006.01)
  *G01T 1/00*   (2006.01)
  *A61B 6/00*   (2006.01)
  *A61N 5/10*   (2006.01)

(52) U.S. Cl.
  CPC .................. *G01T 1/04* (2013.01); *G21F 3/00* (2013.01); *A61B 6/102* (2013.01); *A61B 6/547* (2013.01); *A61N 2005/1094* (2013.01)

(58) Field of Classification Search
  CPC ..... A61B 6/4405; A61B 6/4452; A61B 6/589; A61B 6/0407; A61B 6/4464; A61B 10/0233; A61B 17/3403; A61B 2090/374; A61B 2090/376; A61B 2090/3954; A61B 46/10; A61B 90/39; A61B 17/12022; A61B 17/12109; A61B 17/12113; A61B 17/12145; A61B 17/3415; A61B 2017/1205; A61B 90/11; A61B 6/04; A61B 6/548; A61B 6/022; A61B 6/485; A61B 2090/571; A61B 90/50; A61B 6/032; A61B 6/035; A61B 6/4435; A61B 46/00; A61B 6/06; A61B 6/10; A61B 6/145; A61B 6/4035; A61B 6/4042; A61B 6/4078; A61B 6/482; A61B 6/488; A61B 6/583; A61B 6/587; A61B 2560/0252; A61B 2576/00; A61B 5/0006; A61B 5/0008; A61B 5/0022; A61B 5/0024; A61B 5/0205; A61B 5/02055; A61B 5/02241; A61B 5/02405; A61B 2/02422; A61B 5/0261; A61B 5/0404; A61B 6/037; A61B 6/4488; A61N 2005/1094; A61N 5/1081; A61N 2005/105; A61N 2005/1061; A61N 5/10; G01T 1/00; G01T 1/04; G01T 1/1648; G01T 7/00; G01T 1/20; G01T 1/244; G01T 1/166; G01T 1/249; G01T 1/161; G01T 1/247; G01T 1/295; G01T 7/005; G01T 7/08; G02B 27/02; G02B 27/026; H01J 2229/8911; H01J 2229/8922; H01J 29/867; H01J 29/896; H01J 35/18; G21F 3/00; G21F 1/08; G21F 1/10; G21F 7/00; H04K 1/02; A21C 3/08; A21C 3/10; G21K 1/10; G21K 1/025; G21K 1/02; A61K 2300/00; A61K 36/47; A61K 36/76; A61K 8/35; A61K 8/645; A61K 8/67; A61K 8/9789; G01V 5/0041; G01V 5/005; G01V 5/00; G01V 5/0025; G01V 5/0033; G01V 5/0058; G01V 5/0091; H05K 7/20245; H05K 7/2039; H05K 7/20418; G01N 2223/076; G01N 23/043; G01N 23/20; G01N 23/20083; G01N 23/223; H01L 27/14625; H01L 27/14676; H01L 27/14696
  USPC ........................................................ 378/203
  See application file for complete search history.

(56) References Cited

U.S. PATENT DOCUMENTS

| | | |
|---|---|---|
| 4,837,796 A | 6/1989 | Ema et al. |
| 5,900,638 A * | 5/1999 | Jaeger ................. G21F 3/00 250/519.1 |
| 6,325,538 B1 | 12/2001 | Heesch et al. |
| 6,718,008 B1 | 4/2004 | He et al. |
| 7,057,194 B2 * | 6/2006 | Goldstein ................ G21F 3/00 250/515.1 |
| 7,303,334 B2 * | 12/2007 | Cadwalader .......... A61B 6/107 378/203 |
| 7,331,712 B2 * | 2/2008 | Fischer .................... A61B 6/04 250/519.1 |
| 7,465,947 B2 | 12/2008 | Magram et al. |
| 8,113,713 B2 | 2/2012 | Belson et al. |
| 8,439,564 B2 | 5/2013 | Belson et al. |
| 2009/0232282 A1 | 9/2009 | Belson et al. |

* cited by examiner

50

*{Shielding surroundings from radiation emitted by an X-ray system externally positioned around the periphery of a region of interest located inside an object.}*

52

Providing at least one radiation shield assembly connectable to the X-ray system, the radiation shield assembly includes a support base operatively connectable to a radiation source or a radiation detector of the X-ray system, and a plurality of individually controllable radiation shield segments sequentially positioned around the support base and extendable towards the object.

54

Determining a chosen proximity of a free end of at least one of the radiation shield segments to an opposing portion of the object.

56

Individually actuating, and extending or retracting one or more of the at least one radiation shield segments relative to the support base, until the free end is at the chosen proximity to the opposing portion of the object.

*FIG. 7A*

RADIATION SHIELDING APPARATUSES AND APPLICATIONS THEREOF

CROSS-REFERENCES TO RELATED APPLICATIONS

This application is a continuation of PCT Application No. PCT/US16/61202, filed Nov. 9, 2016, which claims the benefit of priority under 35 USC 119(e) of U.S. Provisional Patent Application No. 62/252,664, filed Nov. 9, 2015, entitled "Radiation Shield Device And Method", and of U.S. Provisional Patent Application No. 62/354,932, filed Jun. 27, 2016, entitled "Radiation Protection Device For X-Ray System Employing Discrete X-Ray Shielding Segments". The contents of these documents are incorporated herein by reference in their entireties.

FIELD OF THE INVENTION

The present invention, in some embodiments thereof, relates to radiation shielding (protecting), and more particularly, but not exclusively, to radiation shielding apparatuses and applications thereof. Exemplary embodiments of the invention relate to apparatuses (devices, systems), and methods, for shielding (protecting) surroundings around the periphery of a region of interest located inside an object (e.g., a patient) from radiation emitted by an X-ray system towards the object. Exemplary embodiments are applicable for shielding (protecting) medical personnel, and patients, from exposure to X-ray radiation during medical interventions or/and diagnostics.

BACKGROUND OF THE INVENTION

A radiation emitting system (for scanning, treatment, or diagnostics) includes a radiation emitting source positioned to oppose one side of an object, and a radiopaque plate or a radiation detector positioned on the opposite side of the object, for example. The radiation emitting source may be any device or mechanism which emits radiation, for example, electromagnetic radiation, such as X-rays or Gamma-rays, and the radiation detector may be any device or mechanism which detects the emitted radiation, including, but not limited, to an image intensifier, an analog circular detector device, and a rectangular digital detector.

In medical imaging applications which include use of an X-ray system, the X-ray system typically generates real-time video or still images of one or more 'regions of interest' within the object (e.g., the body of a subject or patient). Such region(s) of interest is/are considered the areal target for directing the field of view of the X-rays. The X-ray source and the radiation detector are placed on opposite sides of the object (e.g., subject's body), across the region(s) of interest, usually mounted on both ends of a C-shaped arm. Often, the X-ray source is positioned below, and the radiation detector is positioned above, the subject's body. However, for some medical imaging applications, these positions may be reversed, or, alternatively, the X-ray system C-arm may be oriented at essentially any spatially (horizontally or vertically) oblique angle relative to the subject's body.

In such applications, not all radiation emitted by the X-ray source reaches the radiation detector. For example, emitted radiation flux may spread or diffuse around the projection axis, radiation may leak (i.e., leakage radiation) from the X-ray source, or/and radiation may scatter, such as from the X-ray source, the radiation detector or/and from any object in the nearby vicinity of the X-ray source, such as the subject's body or/and the table (bed), or/and any other nearby object(s).

Health care providers, and technical personnel, who operate X-ray systems on a regular basis are usually exposed to a cumulative dosage of radiation, and may be harmed by such cumulative X-ray exposure. In the field and art of medical imaging, there is an on-going need for techniques (equipment and methodologies) applicable for preventing, or at least minimizing, such cumulative radiation exposure, in order to eliminate, or at least reduce, health risks.

Exemplary teachings in the field and art of the invention are provided in the following disclosures by the same applicant/assignee of the present invention: U.S. Pat. Nos. 8,439,564 and 8,113,713, the teachings of which are incorporated by reference as if fully set forth herein.

In spite of these and other teachings in the field and art of the invention, there is on-going need for developing and practicing new or/and improved techniques (apparatuses and methods) of radiation shielding.

SUMMARY OF THE INVENTION

The present invention, in some embodiments thereof, relates to radiation shielding (protecting), and more particularly, but not exclusively, to radiation shielding apparatuses and applications thereof. Exemplary embodiments of the invention relate to apparatuses (devices, systems), and methods, for shielding (protecting) surroundings around the periphery of a region of interest located inside an object (e.g., a patient) from radiation emitted by an X-ray system towards the object. Exemplary embodiments are applicable for shielding (protecting) medical personnel, and patients, from exposure to X-ray radiation during medical interventions or/and diagnostics.

According to an aspect of some embodiments of the present invention, there is provided a radiation protection apparatus for shielding surroundings around the periphery of a region of interest located inside an object from radiation emitted by an X-ray system towards the object, the radiation protection apparatus comprising: at least one radiation shield assembly including a support base operatively connectable to a radiation source or a radiation detector of the X-ray system, and a plurality of radiation shield segments sequentially positioned relative to the support base, thereby forming a contiguous radiopaque screen configured for spanning at least partially around the region of interest periphery with an edge of the radiopaque screen opposing the object; wherein at least one of the radiation shield segments is individually, actively controllable to extend or contract to a selected length with a respective free end thereof in a direction away from or towards the support base, so as to locally change contour of the radiopaque screen edge.

According to some embodiments of the invention, at least one of the radiation shield segments is longitudinally extendible or contractible. Optionally, the free end is positionable relative to other adjacent free ends along a common longitudinal axis.

According to some embodiments of the invention, the radiation protection apparatus further comprises: a control unit, operatively connected to, and configured for controlling operation of, the at least one radiation shield assembly, and the at least one of the radiation shield segments, thereby defining positioning of at least one of the free ends relative to an opposing portion of the object. According to some embodiments of the invention, the control unit determines variable extensions of the radiation shield segments according to the selected length of the at least one of the radiation shield segments.

According to some embodiments of the invention, the radiation protection apparatus further comprises: a drive mechanism, operatively connected to the radiation shield assembly and the control unit, and configured for extending or/and retracting a selected number of the radiation shield segments in accordance with the variable extensions determined by the control unit.

According to some embodiments of the invention, the control unit determines the contour of the radiopaque screen edge correlatively with or/and in response to analysis of a surface curvature of the object.

According to some embodiments of the invention, each of the radiation shield segments is individually extendable or retractable relative to the support base or/and relative to one or more others of the radiation shield segments. According to some embodiments of the invention, each of the radiation shield segments is individually powered by a global power supply, or by a local power supply. According to some embodiments of the invention, the global power supply is configured for globally providing power for operating all components of the radiation protection apparatus. According to some embodiments of the invention, the local power supply is configured for locally providing power for operating a separate unit or group of the radiation shield segments.

According to some embodiments of the invention, the control unit includes a plurality of controllers, each of the controllers is configured for controlling a single separate unit or group of the radiation shield segments. According to some embodiments of the invention, the control unit is configured for globally controlling all separate units or groups of the radiation shield segments.

According to some embodiments of the invention, the drive mechanism includes a plurality of drivers, each of the drivers is configured for extending or/and retracting a single separate unit or group of the radiation shield segments. According to some embodiments of the invention, the drive mechanism is configured for globally extending or/and retracting all separate units or groups of the radiation shield segments.

According to some embodiments of the invention, the radiation source and the radiation detector define a beam axis extending therebetween, wherein each of the radiation shield segments is configured to be structurally rigid so as to retain a maximally extended shape along an extension axis that forms an elevation angle relative to direction of gravitational force acting upon the maximally extended shape. According to some embodiments of the invention, the elevation angle is 15 degrees or more, optionally particularly 30 degrees or more, optionally particularly 45 degrees or more, optionally particularly 90 degrees or more.

According to some embodiments of the invention, the radiation protection apparatus further comprises a sensing unit operatively connected to the at least one radiation shield assembly. According to some embodiments of the invention, the sensing unit includes at least one positioning sensor coupled to at least one of the radiation shield segments and configured to sense and react to positioning or proximity of the at least one free end relative to the opposing portion of the object, or to a contact therebetween. According to some embodiments of the invention, the sensing unit includes at least one radiation detecting sensor configured to detect a portion of the radiation emitted by the radiation source and leaking through the plurality of radiation shield segments.

According to some embodiments of the invention, the sensing unit is operatively connected to, and configured for providing data-information to, the control unit, whereby the control unit is responsive to the data-information provided by the sensing unit.

According to some embodiments of the invention, each of the radiation shield segments comprises a plurality of overlapping radiopaque tiles, wherein extending and retracting of the radiation shield segments respectively decreases and increases extent of overlap between the radiopaque tiles.

According to some embodiments of the invention, the radiation protection apparatus further comprises a data-information processing unit, operatively connected to, and configured for processing data-information associated with, the at least one radiation shield assembly and the control unit. According to some embodiments of the invention, the data-information processing unit is configured for determining reactive actuation parameters of at least one other of the radiation shield segments in response to the relative positioning of the at least one free end. According to some embodiments of the invention, the relative positioning relates to a maximally or/and minimally allowable distance between the free end and the opposing portion of the object. According to some embodiments of the invention, the relative positioning relates to a maximally allowable force measured when forcing the free end against the opposing portion of the object.

According to some embodiments of the invention, the control unit is configured for controlling reactive actuation of at least one other of the radiation shield segments in response to the relative positioning of the at least one free end. According to some embodiments of the invention, extension of at least one other of the radiation shield segments changes, via the reactive actuation, in relation to a predetermined ratio of the extension and extension of the at least one of the radiation shield segments.

According to some embodiments of the invention, at least one other of the radiation shield segments fully retracts in response to the reactive actuation.

According to some embodiments of the invention, the radiation protection apparatus comprises a first radiation shield assembly including a first support base operatively connectable to the radiation source, and a second radiation shield assembly including a second support base operatively connectable to the radiation detector.

According to some embodiments of the invention, the radiation protection apparatus further comprises an optical capturing device configured to capture images of at least some of the radiation shield segments or/and of the object.

According to some embodiments of the invention, at least one free end is connected to a flexible spacer. According to some embodiments of the invention, the flexible spacer is configured to individually move relative to the at least one free end. According to some embodiments of the invention, the flexible spacer is configured to move according to at least one moving mode of bending, rotating, pivoting, and shifting away from alignment with the radiation shield segment connected thereto. According to some embodiments of the invention, the flexible spacer is configured such that the individual relative movement is facilitated in reaction to compressing against the object or/and conforming to the surface curvature of the object. According to some embodiments of the invention, the flexible spacer is configured to move according to a pre-calculated relative movement determined before contacting opposing boundary of the object. According to some embodiments of the invention, the flexible spacer is radiopaque to the radiation emitted by the X-ray system. According to some embodiments of the invention, the flexible spacer is configured for spacing or/and compressing between the at least one free end and relative to an opposing portion of the object, or/and to conform to a surface curvature of the object.

According to some embodiments of the invention, at least one of the radiation shield segments includes: a radiopaque cover member ending with a cover member free end; a length dispenser operatively connected to the support base, the length dispenser is configured for covering a sector around the support base, and for controlling cover member length extending between the length dispenser and the cover member free end; and a first frame member operatively connected, via a first end thereof, to the length dispenser, and operatively connected, via a second end thereof, to the cover member free end, the first frame member is extendible or contractible according to control of the cover member length, and maintains structural rigidity sufficient for supporting the cover member in a laterally straight form along a chosen cover member deployed length.

According to some embodiments of the invention, the cover member is configured in a form of a roller-shade such that a remaining non-deployed length of the cover member is rolled inside of the dispenser. According to some embodiments of the invention, the cover member is configured in a form of strips or tiles with selectively changeable overlapping, such that the cover member deployed length decreases by increasing overlapping between the strips or tiles.

According to some embodiments of the invention, the drive mechanism is configured to force the cover member or/and the first frame member to extend or contract when shifting from the chosen cover member deployed length.

According to some embodiments of the invention, the first frame member includes a plurality of first frame sections telescopically arranged and slidable inside one another or alongside one another. According to some embodiments of the invention, the first frame member extends along the cover member deployed length, thereby covering a first side of the cover member.

According to some embodiments of the invention, the radiation protection apparatus further comprises a second frame member extendible or contractible along the chosen cover member deployed length and above a second side of the cover member, opposing the first side thereof.

According to some embodiments of the invention, the radiation protection apparatus comprises a first and a second of the radiation shielding segments, juxtapositionally arranged, wherein the first radiation shielding segment is equipped with a first the cover member supported with the first frame member along a first adjacent side thereof, and the second radiation shielding segment is equipped with a second the cover member supported with the second frame member along a second adjacent side thereof, whereby the first radiation shielding segment adjacent side lies adjacent to the second radiation shielding segment adjacent side.

According to some embodiments of the invention, the first frame member includes a lateral extension sized for covering a gap spanning between the first radiation shielding segment adjacent side and the second radiation shielding segment adjacent side, or/and for covering the second radiation shielding segment adjacent side. According to some embodiments of the invention, the second frame member is sized and shaped for mating against the lateral extension of the adjacent first frame member. According to some embodiments of the invention, the first frame member is slidably interconnected with the adjacent second frame member.

According to an aspect of some embodiments of the present invention, there is provided an X-ray system comprising: a radiation source configured to emit radiation that is transmitted through an object and towards a radiation detector; and at least one radiation shield assembly comprising: a support base operatively connected to the radiation source or/and the radiation detector, and a plurality of individual radiation shield segments sequentially positioned relative to the support base; wherein each of the radiation shield segments is controllably, variably extendable or retractable between the radiation source or/and the radiation detector and the object.

According to some embodiments of the invention, in the X-ray system, the plurality of radiation shield segments is configured for forming a contiguous radiopaque screen spanning at least partially around the X-ray system.

According to an aspect of some embodiments of the present invention, there is provided a method of shielding surroundings from radiation emitted by an X-ray system externally positioned around the periphery of a region of interest located inside an object, the method comprising: providing at least one radiation shield assembly connectable to the X-ray system, the radiation shield assembly includes a support base operatively connectable to a radiation source or a radiation detector of the X-ray system, and a plurality of individually controllable radiation shield segments sequentially positioned relative to the support base and extendable towards the object; determining a chosen proximity of a free end of at least one of the radiation shield segments to an opposing portion of the object; and individually actuating, and extending or retracting one or more of the at least one radiation shield segments relative to the support base, until the free end is at the chosen proximity to the opposing portion of the object.

According to some embodiments of the invention, the method further comprises: repeating the determining and the individual actuating of the at least one of the radiation shield segments, or/and of one or more others of the radiation shield segments, until collectively forming a contiguous radiopaque screen spanning at least partially around the periphery of the region of interest with an edge contoured correlatively with a surface curvature of the object.

According to some embodiments of the invention, the determining is performed by using at least one positioning sensor configured for detecting positioning of at least one of the radiation shield segments relative to the object.

According to some embodiments of the invention, the individually actuating is performed by using a drive mechanism configured for extending or/and retracting a selected number of the radiation shield segments in correlation to the position detecting.

According to some embodiments of the invention, the method further comprises: using at least one radiation detecting sensor configured for detecting a portion of the radiation emitted by the radiation source and leaking through the contiguous radiopaque screen.

According to some embodiments of the invention, the individually actuating is performed by using a drive mechanism configured for extending or/and retracting a selected number of the radiation shield segments in correlation to the radiation detecting.

According to some embodiments of the invention, the determining is performed by using a data-information processing unit configured for processing data-information associated with the at least one radiation shield assembly.

All technical or/and scientific words, terms, or/and phrases, used herein have the same or similar meaning as commonly understood by one of ordinary skill in the art to which the invention pertains, unless otherwise specifically defined or stated herein. Exemplary embodiments of technology, methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

Implementation of some embodiments of the invention can involve performing or completing selected tasks manually, automatically, or a combination thereof. Moreover, according to actual instrumentation and equipment of some embodiments of the invention, several selected tasks could be implemented by hardware, by software, by firmware, or a combination thereof, using an operating system.

BRIEF DESCRIPTION OF THE SEVERAL VIEW OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings:

FIG. 1 schematically illustrates an exemplary C-arm type X-ray system that is suitable for implementing exemplary embodiments of the present invention, according to some embodiments of the invention;

FIG. 2 schematically illustrates an exemplary radiation protection apparatus operatively connected to (and mounted on) an exemplary X-ray system, according to some embodiments of the invention;

FIG. 3 schematically illustrates a plurality of exemplary radiation shield segments which may be included in exemplary embodiments of the radiation shield assembly of the radiation protection apparatus, highlighting the plurality of radiation shield segments forming a contiguous radiopaque screen with an edge contoured correlatively with a surface curvature of an object (subject), according to some embodiments of the invention;

FIG. 4 schematically illustrates another exemplary embodiment of the radiation protection apparatus, highlighting exemplary apparatus components and operative connections thereof, according to some embodiments of the invention;

FIG. 5 schematically illustrates another exemplary embodiment of the radiation protection apparatus, highlighting exemplary apparatus components and operative connections thereof, according to some embodiments of the invention;

FIGS. 6A-6C schematically illustrate an exemplary radiation protection apparatus positioned at different exemplary elevation angles, according to some embodiments of the invention;

FIG. 7A is a flow diagram of an exemplary embodiment of a method of shielding surroundings from radiation emitted by an X-ray system externally positioned around the periphery of a region of interest located inside an object, according to some embodiments of the invention;

Figure 8A:
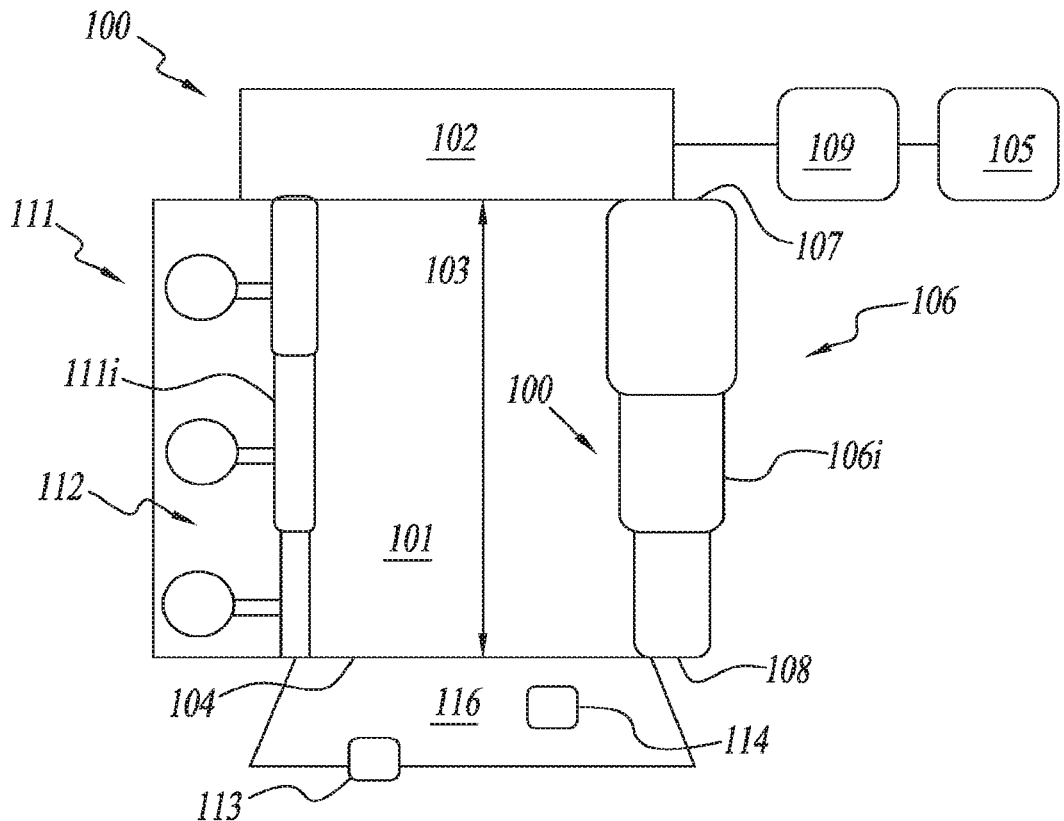
Figure 8B:
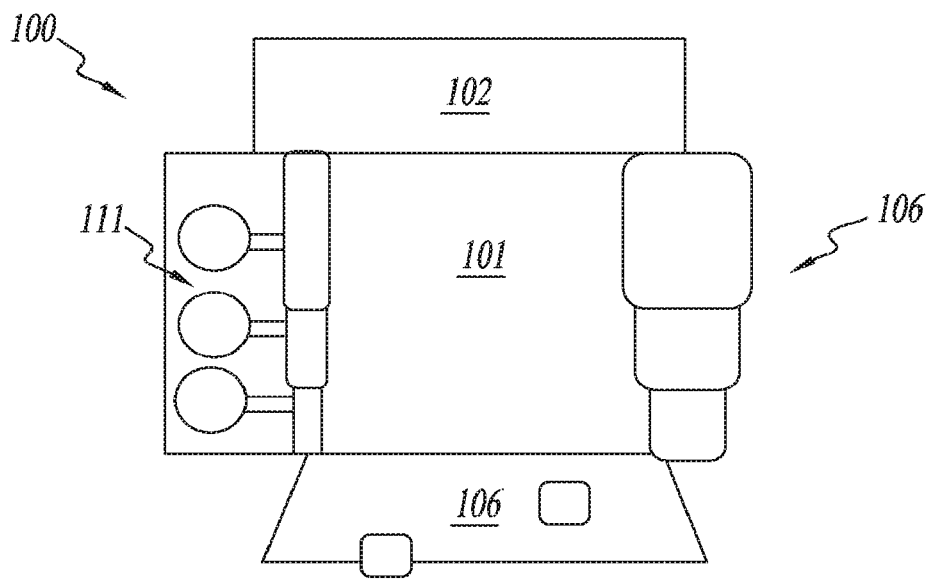
Figure 9A:
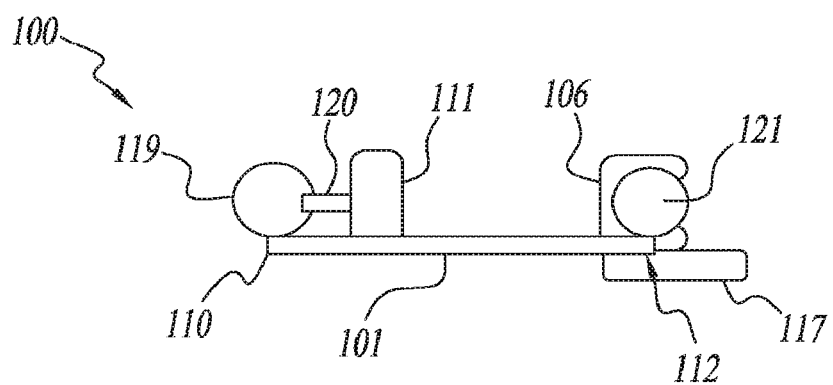
Figure 9B:
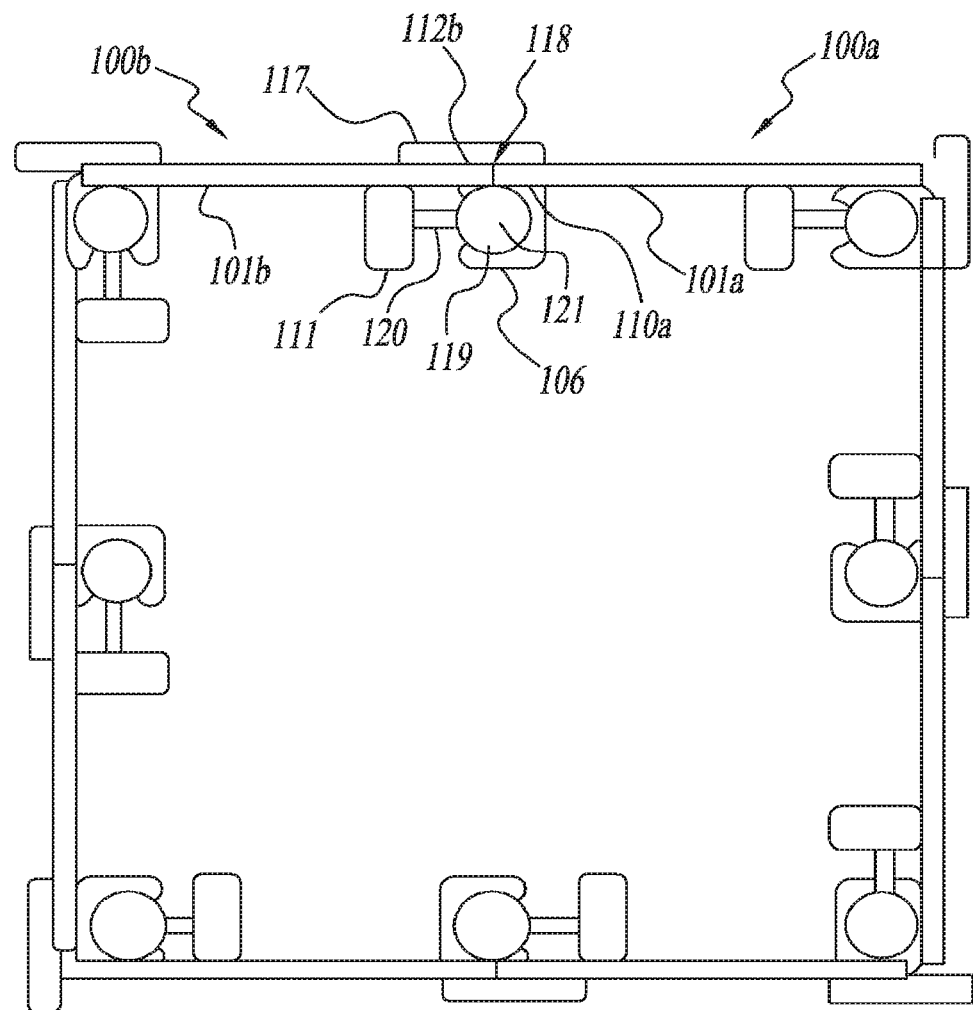
Figure 11A:
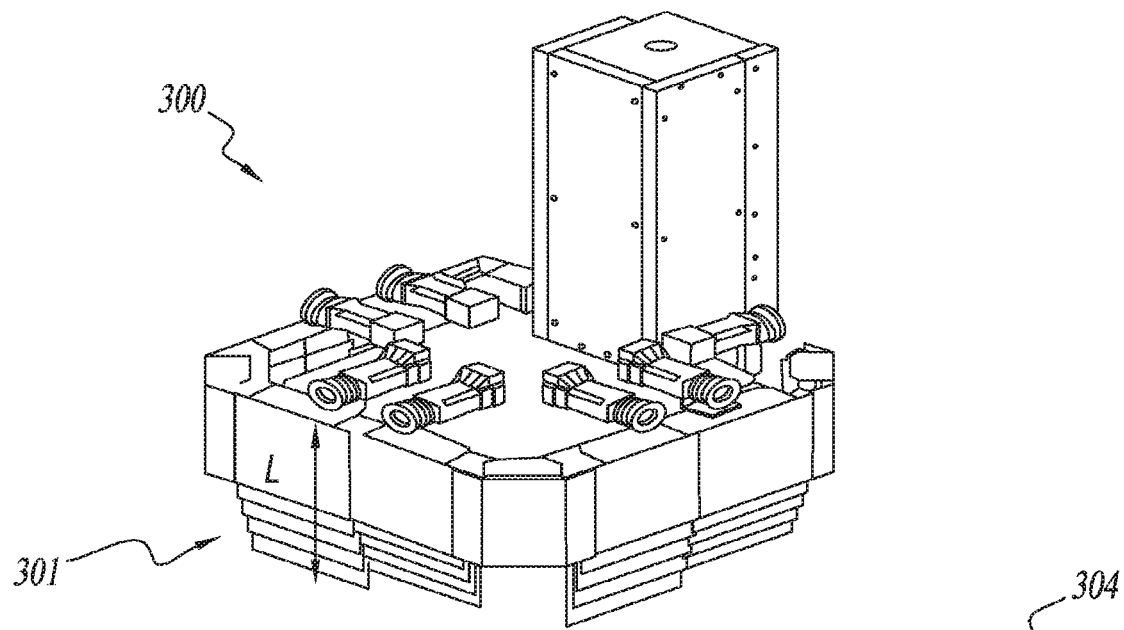
Figure 11B:
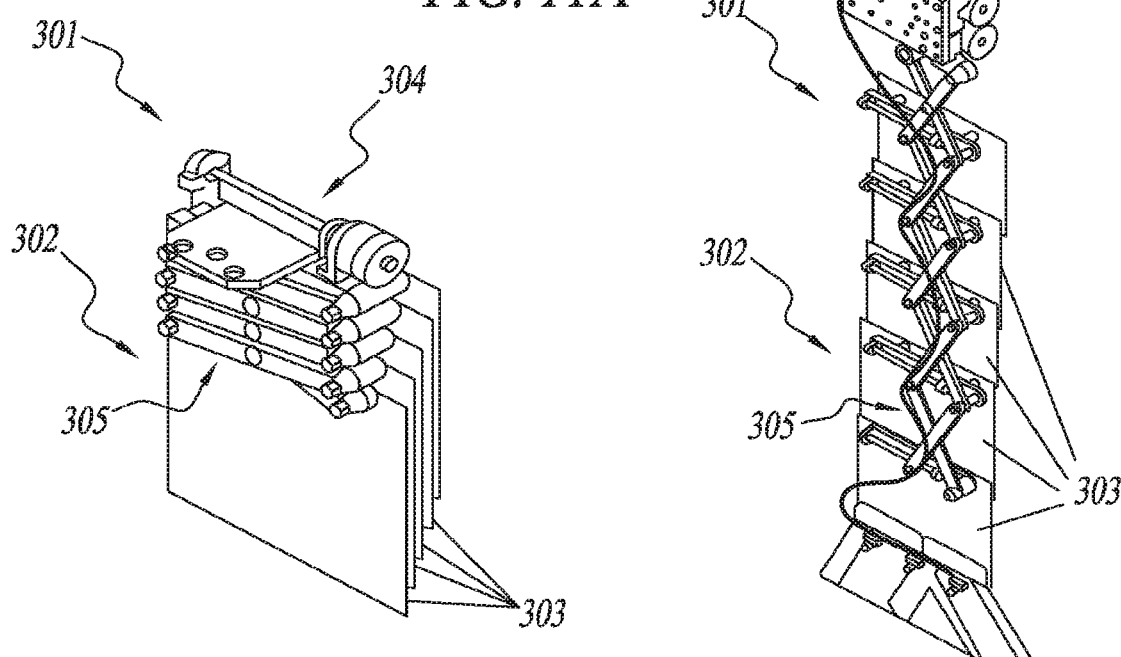
Figure 11C:
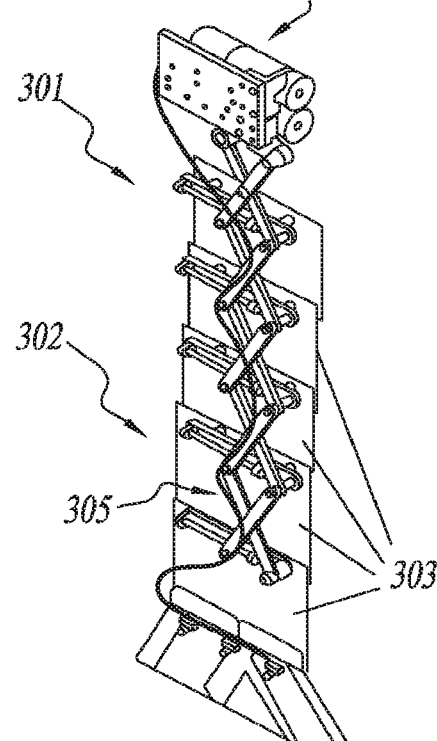
Figure 12A:
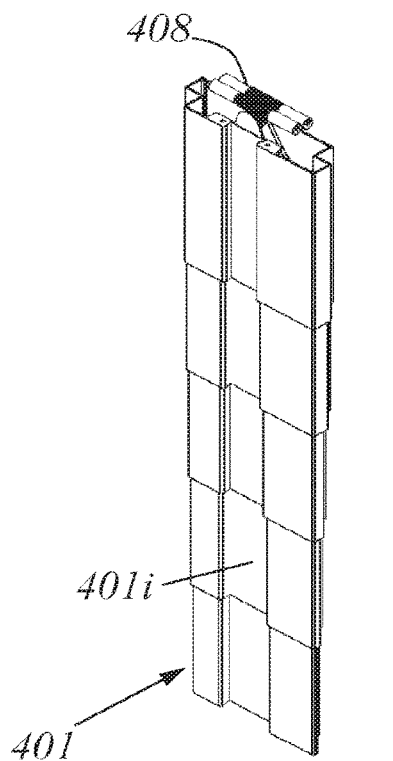
Figure 12B:
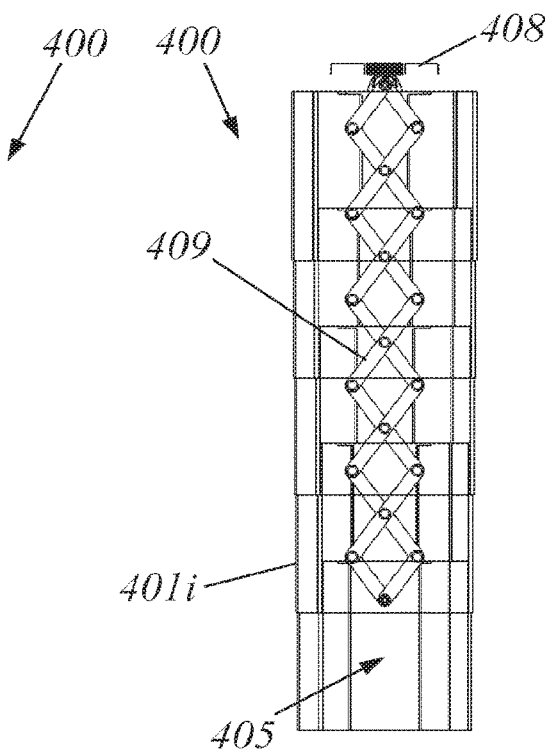
Figure 12C:
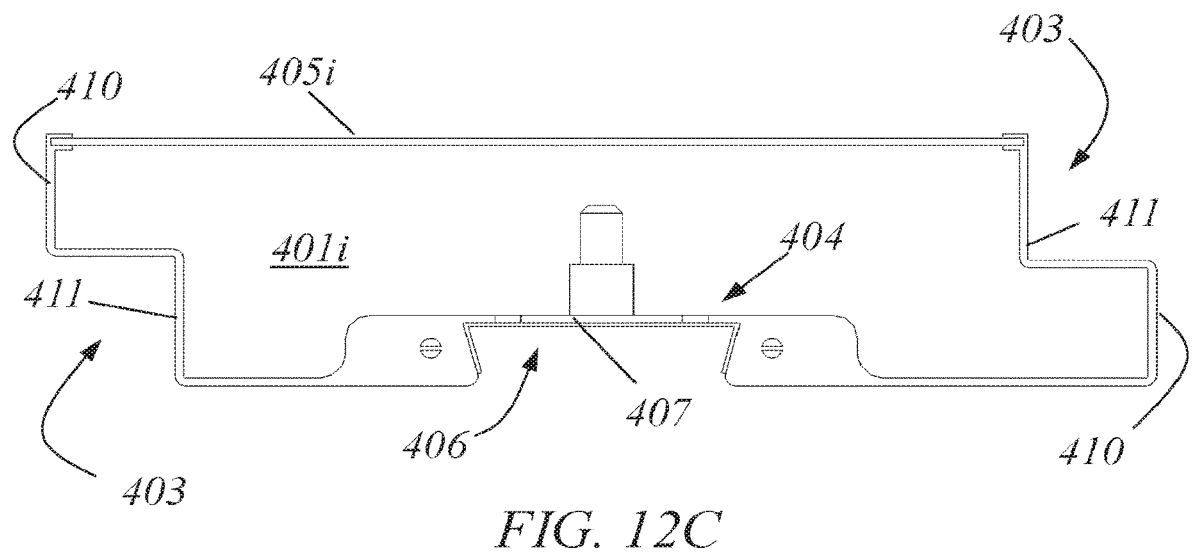
Figure 12E:
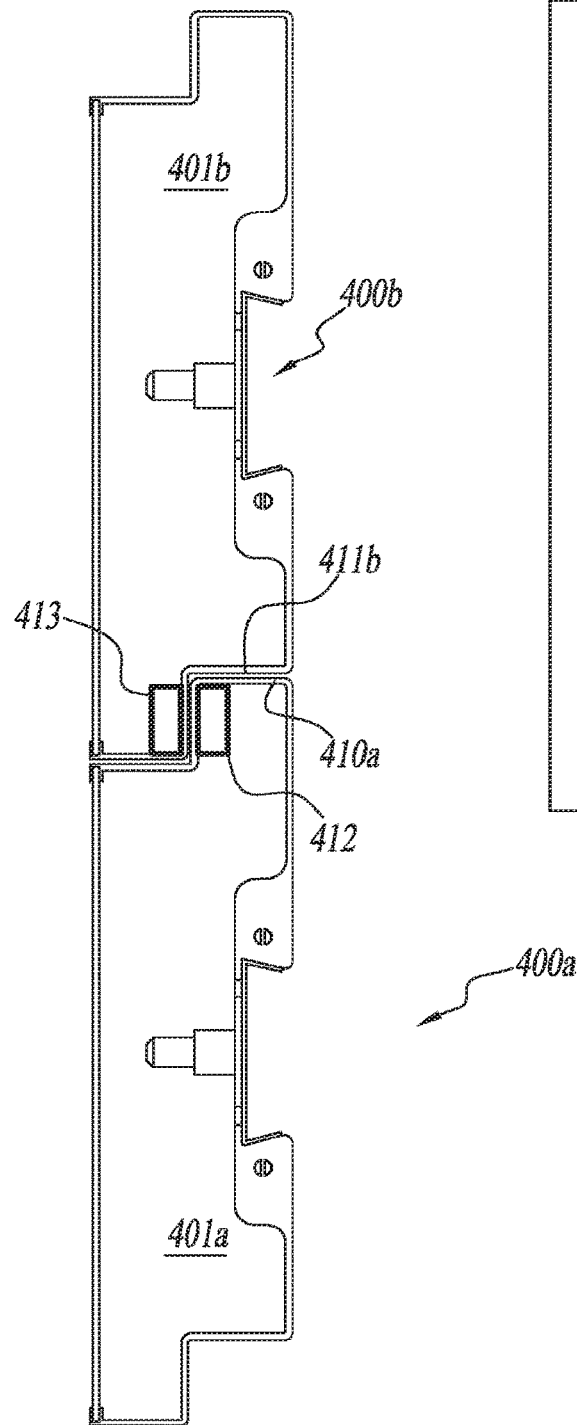
Figure 12D:
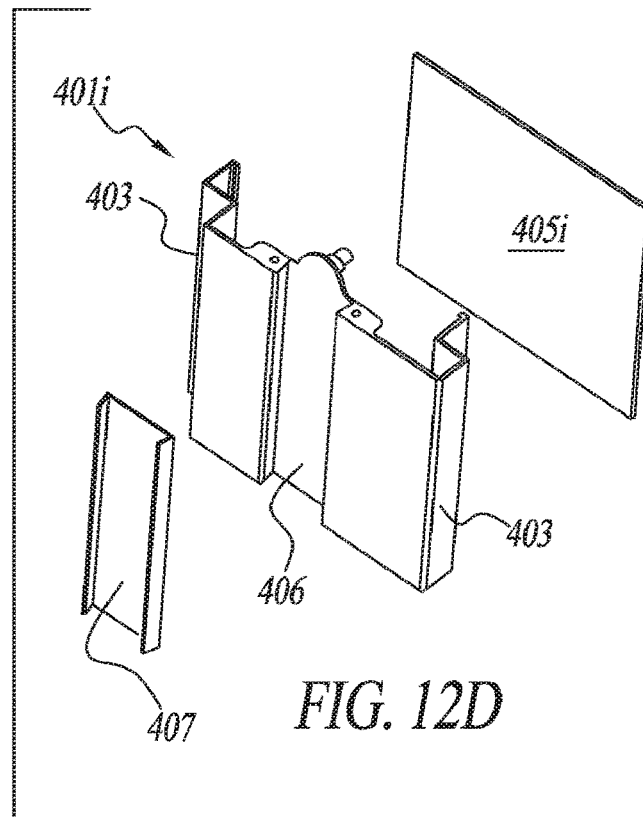
Figure 13A:
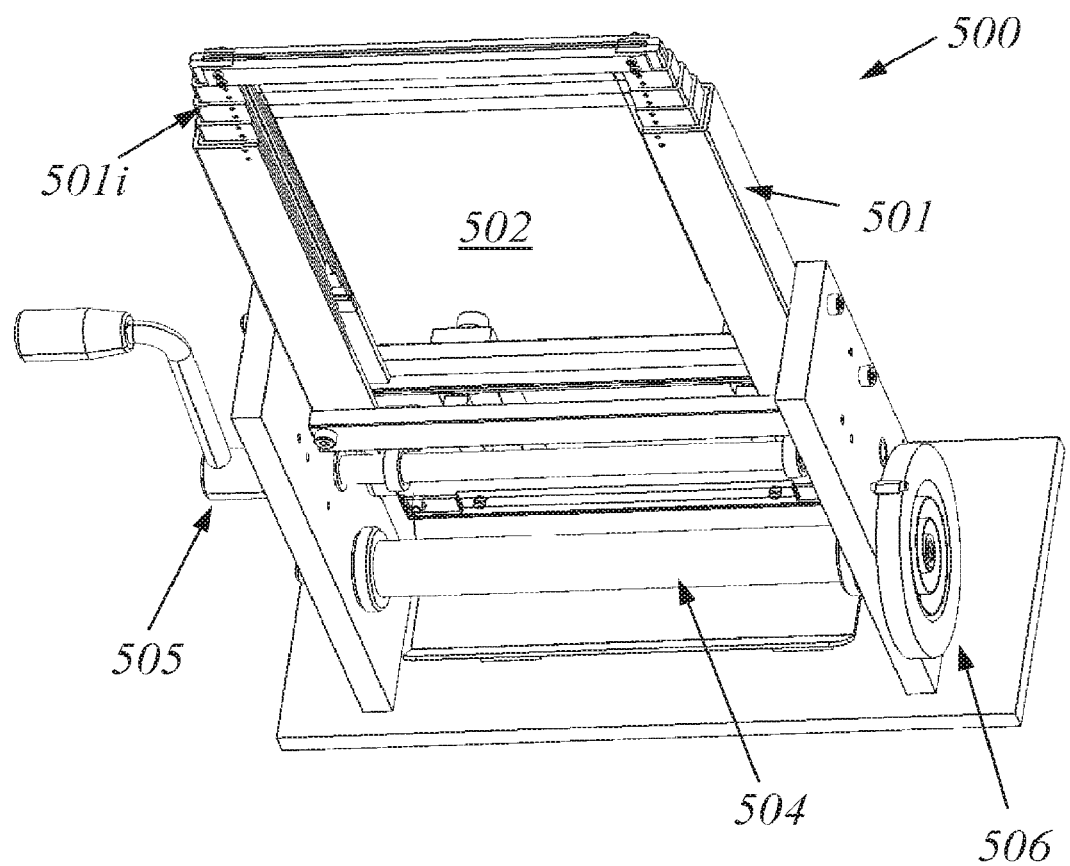
Figures 13B, 13C:
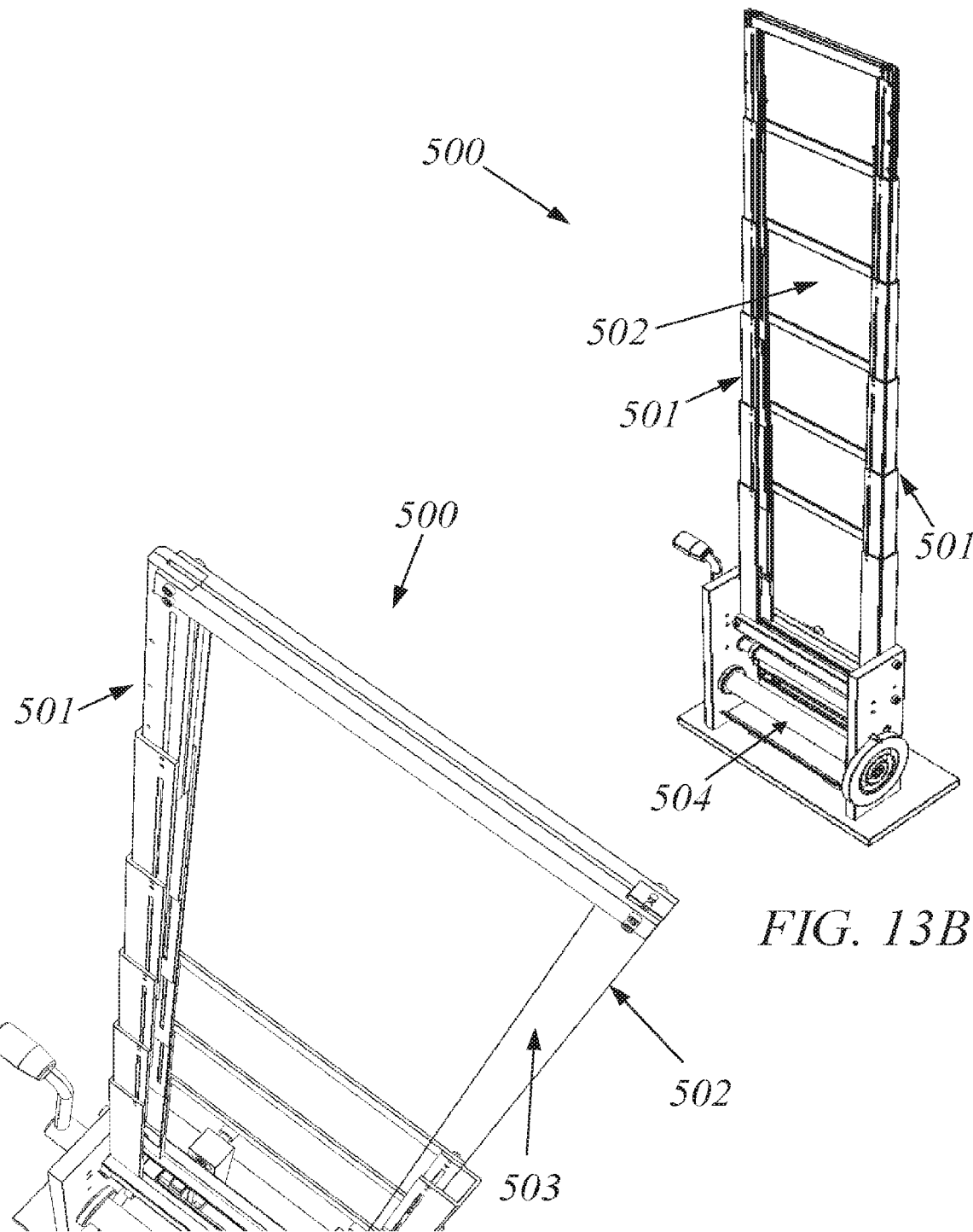

FIGS. 8A-8B schematically illustrate side views of an exemplary (discrete) radiation shield segment of an exemplary radiation protection apparatus, according to some embodiments of the invention;

FIGS. 9A-9B schematically illustrate top views of an exemplary (discrete) radiation shield segment and an exemplary assembly of such (discrete) radiation shield segments, according to some embodiments of the invention;

FIGS. 10A-10H schematically illustrate an exemplary X-ray system to which is operatively connected (and mounted) an exemplary radiation protection apparatus including a plurality of exemplary discrete radiation shield segments having a radiopaque cover member in a form of a roller-shade, and assemblies thereof, according to some embodiments of the invention;

FIGS. 11A-11C schematically illustrate an exemplary radiation shield assembly including a plurality of exemplary discrete radiation shield segments having a radiopaque cover member in a form of overlapping tiles, and assembly thereof, according to some embodiments of the invention;

FIGS. 12A-12E schematically illustrate an exemplary (discrete) rigid radiation shield segment, each including a single (embedded) frame member, and suitable for inclusion in the radiation shield assembly, according to some embodiments of the invention; and FIGS. 13A-13C schematically illustrate an exemplary discrete radiation shield segment operational with an exemplary push-strip, according to some embodiments of the invention.

DESCRIPTION OF SPECIFIC EMBODIMENTS OF THE INVENTION

The present invention, in some embodiments thereof, relates to radiation shielding (protecting) apparatuses and applications thereof. Exemplary embodiments of the invention relate to apparatuses (devices, systems), and methods, for shielding (protecting) surroundings around the periphery of a region of interest located inside an object (e.g., a patient) from radiation emitted by an X-ray system towards the object. Exemplary embodiments are applicable for shielding (protecting) medical personnel, and patients, from exposure to X-ray radiation during medical interventions or/and diagnostics.

In medical imaging applications involving use of an X-ray system, not all radiation emitted by the X-ray source reaches the radiation detector, whereby some of the emitted X-ray radiation may impinge upon human subjects (e.g., health care providers, technical personnel, patients). Such exposure of human subjects to emitted X-ray radiation may cause substantially harmful health effects, especially, when exposure occurs on a repetitive basis, particularly, over long periods of time. In such medical imaging applications, there is an on-going need for techniques (equipment and methodologies) applicable for preventing, or at least minimizing, exposure of subjects to radiation exposure, in order to eliminate, or at least reduce, health risks.

The term 'X-ray system', as used herein, in a non-limiting manner, refers to any radiography or radiotherapy X-ray emitting type system, such as digital radiology, fluoroscopy, or digital X-ray systems. X-ray system also refers to X-ray emitting type systems suitable for use in non-medical applications, such as security related applications.

For purposes of further understanding exemplary embodiments of the present invention, in the following illustrative description thereof, reference is made to the figures (FIGS. 1 through 13). Throughout the following description and accompanying drawings, same reference numbers refer to same components, elements, or features. It is to be understood that the invention is not necessarily limited in its application to particular details of construction or/and arrangement of exemplary device, apparatus, or/and system components, set forth in the following illustrative description. The invention is capable of other exemplary embodiments or of being practiced or carried out in various ways.

Figure 1:
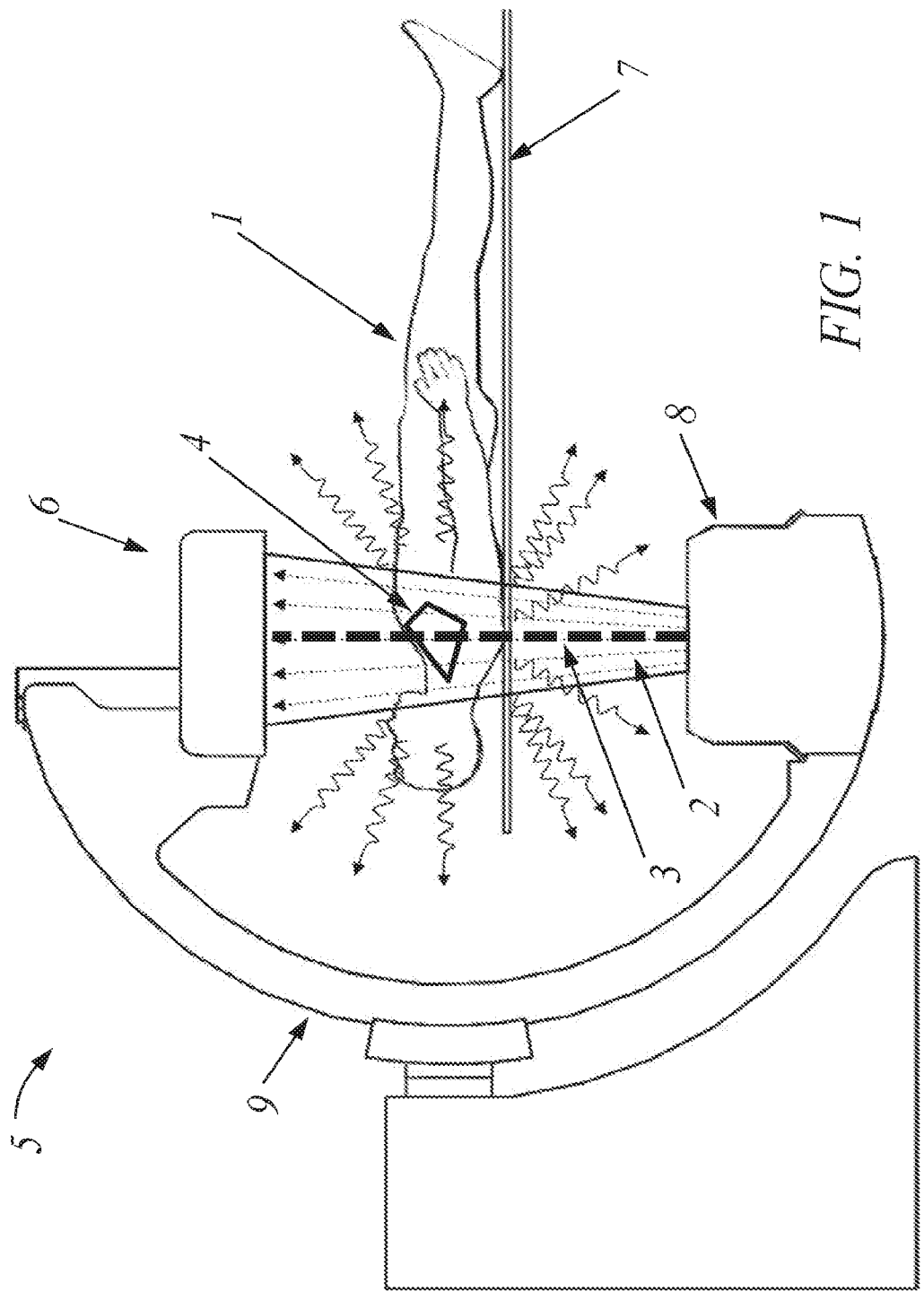

FIG. 1 schematically illustrates an exemplary C-arm type X-ray system 5 that is suitable for implementing exemplary embodiments of the present invention. X-ray system 5 includes a radiation source 8 and a radiation detector 6 mounted on opposite ends of a C-arm 9. C-arm 9 may be mounted on a mobile base with wheels or it may be mounted via a support arm to the floor or the ceiling of a fluoroscopy suite, or in any other manner. The object for the X-ray system operation is a subject 1 resting on a table 7. Subject 1 may refer to an entire human person or animal or to a portion (e.g. limb) thereof. Nevertheless, X-ray system 5 may be configured to scan any other type of object, including artifacts (for applications related to border control and customs, for example).

In use, the radiation source 8 and radiation detector 6 are placed on opposite sides of the body of subject 1, for example, across a requested region of interest 4. Radiation source 8 emits an X-ray beam 2 that passes through the imaged object toward the radiation detector 6, which records the exposure to X-ray radiation and sends the image or video feed to a computer or/and display either in real time, or at a later time. Often, radiation source 8 is positioned below the patient and the detector 6 is positioned above, as shown, however for some applications these positions may be reversed or the C-arm 9 may be oriented at any spatially oblique angle. Beam 2 travels generally (in a conic dispersion) along a straight beam axis 3 which is geometrically defined as the line segment between the center of radiation source 8 and center of radiation detector 6, although not all emitted radiation reaches detector 6 and a residual dosage is commonly scattered at different angles, usually from subject 1 or table 7.

Exemplary embodiments of the present invention relate to a radiation protection apparatus for shielding surroundings around the periphery of a region of interest 4 located inside an object (subject 1) from radiation emitted by an X-ray system (e.g., X-ray system 5) towards the object. In some embodiments, the radiation protection apparatus is structurally configured to operate at different angles around the object (subject 1) without loss of functionality. In exemplary embodiments, the radiation protection apparatus includes a radiation shield assembly having a plurality of radiation shield segments. In such embodiments, each of the radiation shield segments is optionally configured to be structurally rigid so as to retain a maximally extended shape along an extension axis that forms an elevation angle relative to the direction of gravitational force acting upon such a maximally extended shape. In exemplary embodiments, the elevation angle may be 15 degrees or more, optionally particularly 30 degrees or more, optionally particularly 45 degrees or more, optionally particularly 90 degrees or more.

An aspect of some embodiments of the invention is provision of a radiation protection apparatus for shielding surroundings around the periphery of a region of interest located inside an object from radiation emitted by an X-ray system towards the object. In exemplary embodiments, the radiation protection apparatus includes: at least one radiation shield assembly including a support base operatively connectable to a radiation source or a radiation detector of the X-ray system, and a plurality of radiation shield segments sequentially positioned relative to the support base, thereby forming a contiguous radiopaque screen configured for spanning at least partially around the region of interest periphery with an edge of the radiopaque screen opposing the object. In exemplary embodiments, at least one of the radiation shield segments is individually, actively controllable to extend or contract to a selected length with a respective free end thereof in a direction away from or towards the support base, so as to locally change contour of the radiopaque screen edge.

Figure 2:
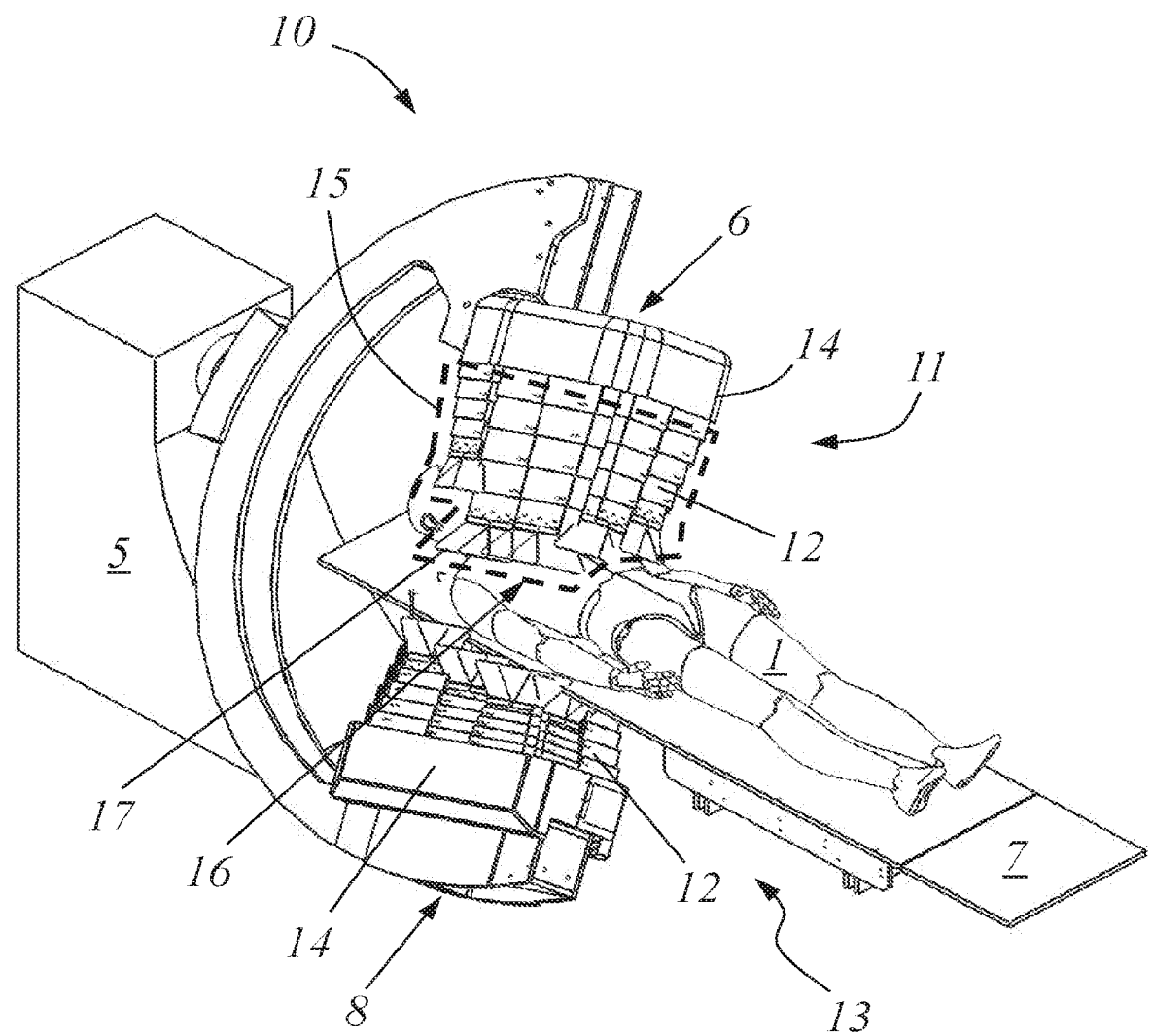

FIG. 2 schematically illustrates exemplary radiation protection apparatus 10 operatively connected to (and mounted on) exemplary X-ray system 5. Radiation protection apparatus 10 includes a first radiation shield assembly 11 disposed in a region of space between radiation detector 6 and table 7, and a second radiation shield assembly 13 disposed in a region of space between source 8 and table 7. Nevertheless, only a single radiation shield assembly may be used as part of radiation protection apparatus 10, for example in the region next to source 8 only. At least one radiation shield assembly (11 or/and 13) includes a support base 14 operatively connectable to radiation source 8 or radiation detector 6 of X-ray system 5. Support base 14 is optionally circumferential (e.g., in a form of ellipse, such as a circle, or in a form of tetragon, such as a parallelogram or a rectangle), although it may capture only one side or sector around radiation source 8 or radiation detector 6.

A plurality of radiation shield segments 12 are sequentially positioned relative to support base 14, thereby forming a contiguous radiopaque screen 15 configured for spanning at least partially around the region of interest 4 periphery with a radiopaque screen edge 16 opposing the object (subject 1). In some embodiments, at least one of the radiation shield segments 12 is individually, actively controllable to extend or contract to a selected length with a respective free end 17 thereof in a direction away from or towards support base 14, so as to locally change contour of radiopaque screen edge 16. In some embodiments, each of the at least one of the radiation shield segments 12 is longitudinally extendible or contractible along a longitudinal axis of the respective radiation shield segment 12. In exemplary embodiments, the free end 17 of a respective radiation shield segment 12 is positionable relative to other adjacent free ends 17 along a common longitudinal (straight) axis.

Figure 3:
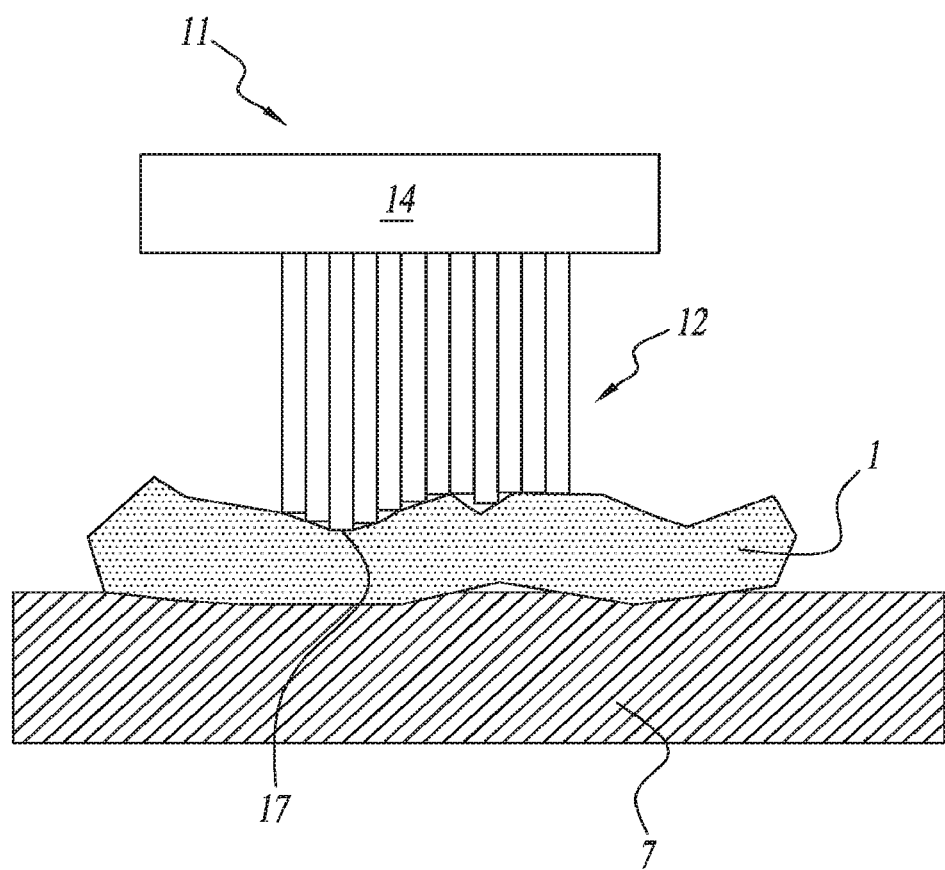

FIG. 3 schematically illustrates a plurality of exemplary radiation shield segments which may be included in exemplary embodiments of the radiation shield assembly, which, in turn, is included in exemplary embodiments of the radiation protection apparatus. In exemplary embodiments, the plurality of radiation shield segments is configured for forming a contiguous radiopaque screen with an edge contoured correlatively with a surface curvature of an object (subject). Theoretically, there is no limit on the number of radiation shield segments included in the radiation shield assembly. For example, the radiation shield assembly may include at least 1, or at least 2, or at least 3, or at least 4, or at least 5, or at least 10, or at least 15, or at least 20, radiation shield segments. In some embodiments, and as shown in FIG. 3, it may be advantageous to provide a greater number of radiation shield segments in order to increase accuracy (resolution) and close matching with free 17 ends can more closely match a surface curvature of the object. By providing the degree of freedom where the radiation shield segments are individually extendable (i.e. rather than constraining them so that differences in extensions of the radiation shield segments are fixed), this allows the 'multi-segment' shield assembly 11 to be operated so that the degree of extension of each segment closely matches an opposing surface (e.g. upper surface of subject 1) in a manner that minimizes the distance between the two.

In many situations (e.g. where the upper surface of the subject 1 is quite irregular) this allows for an almost 'seal' between the upper surface of the subject 1 and contour of radiopaque screen edge 16, and therefore increases the effectiveness of the shields.

By providing the degree of freedom where the radiation shield segments are individually extendable (i.e. rather than constraining them so that differences in extensions of the radiation shield segments are fixed), this allows the multi-segment shield to be operated so that the degree of extension of each segment closely matches an opposing surface (e.g. upper surface of subject 1) in a manner that minimizes the distance between the two. In some embodiments, it is possible for a user to manually configure the radiation shield segments 12 to a specific multi-extension-state of the multi-extension-state space. Alternatively or additionally, radiation shield 12 further includes a motorized system modifying degrees-of-extensions (e.g. measureable, for example, by a distance between a distal location of the radiation shield segment and a base location).

In one example, each radiation shield segment 12 is associated with a different respective motor for moving the distal edge along beam axis 3 to increase (or decrease) an extension of the radiation shield segment. In another example, a single common motor suffices, and, for example, each radiation shield segment may be associated with a different respective clutch, and all clutches are associated with the common motor.

In some embodiments, a sensor unit is provided to determine, for at least some of radiation shield segments, at least one of (i) a respective proximity between a respective fixed location on the radiation shield segment (e.g. distal end of a radiation shield segment) and a target surface; and (ii) an extent of contact between the respective distal end of the radiation shield segment and an opposing surface.

In some embodiments, the output from the sensors may be used (e.g. via a control unit) to determine the extent of extension or retraction needed for one or more of the segments of one or more of the shields. Thus, in one non-limiting example, (i) at least one shield 12 starts out in retracted configuration and (ii) the motorized system extends each segment towards an opposing surface (e.g. an upper surface of subject 1, or a surface of table 7) until the segment contacts (or nearly contacts—e.g. within a distance of at most 15 cm or at most 10 cm or at most 3 cm or at most 2 cm or at most 1 cm or at most 5 mm or at most 3 mm or at most 1 mm) the opposing surface. In this case, sensor system measures the distance between a respective distal end of each radiation shield segment and in response to the output of the sensor unit, the motorized system continues to extend each radiation shield segment 12 until a distal end of the radiation shield segment respectively reaches the desired position.

Figure 4:
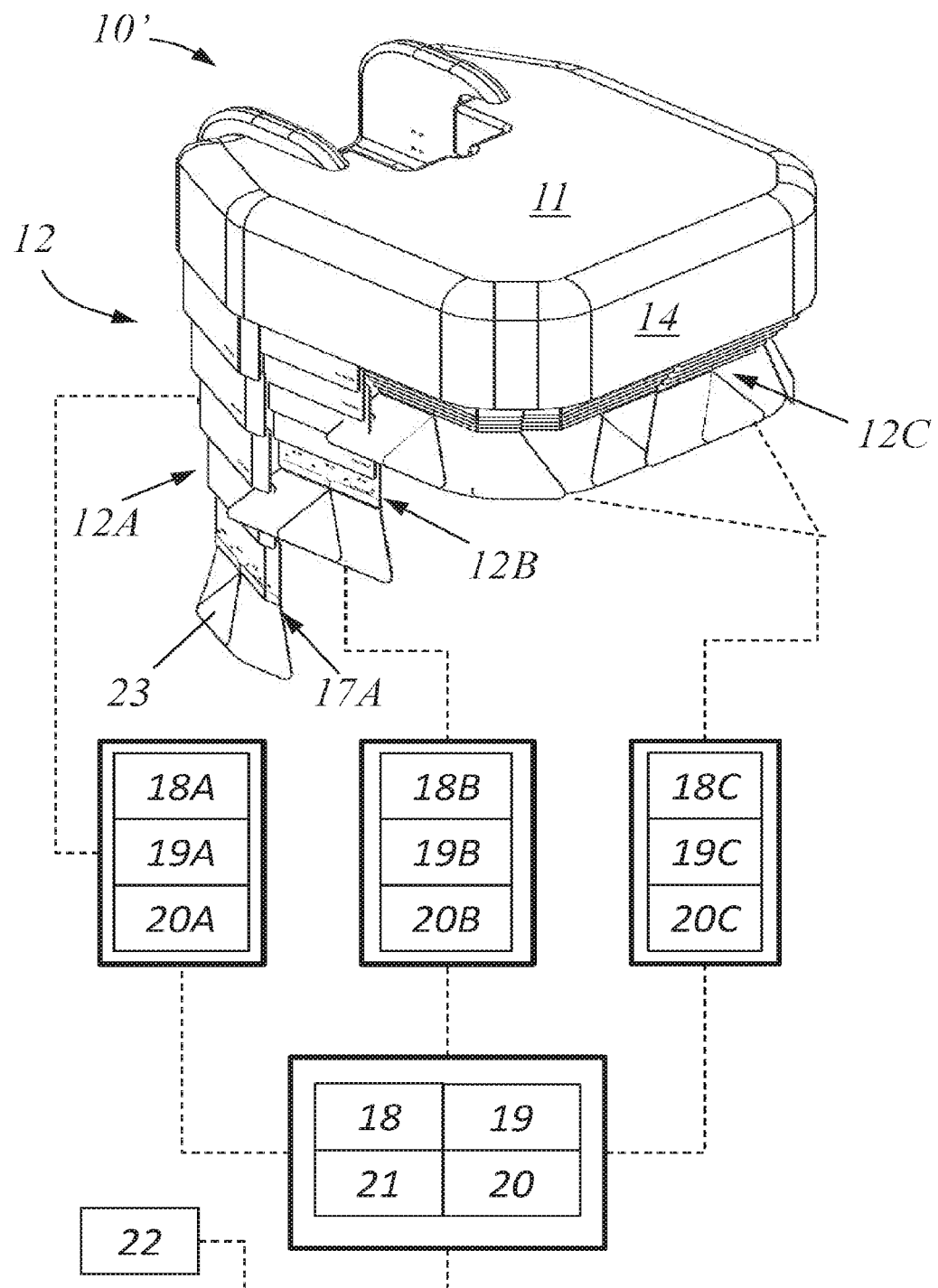

FIG. 4 schematically illustrates another exemplary embodiment of the radiation protection apparatus, and referenced as exemplary radiation protection apparatus 10', highlighting exemplary apparatus components and operative connections thereof. Exemplary radiation protection apparatus 10' corresponds to exemplary radiation protection apparatus 10 equipped with first radiation shield assembly 11 (although it may be equipped, also or instead, with second radiation shield assembly 13, for example). Radiation protection apparatus 10' includes a control unit 18, operatively connected to, and configured for controlling operation of, first (or/and second) radiation shield assembly 11, and at least one of radiation shield segments 12, thereby defining positioning of at least one of free ends 17 relative to an opposing portion of the object (e.g., subject 1). Control unit 18 determines variable extensions of radiation shield segments 12 according to the selected length of the at least one of radiation shield segments 12. In this example, first radiation shield assembly 11 is shown in a particular setting configured for only partial angular coverage, which is less than 360 degrees, for example in order to avoid contact with patient's head or face. Each discrete radiation shield segment 12 is individually extendable or retractable from a location of support base 14. The presence of multiple segments that are individually extendable offers an additional degree-of-freedom—instead of the relative extension of each segment being fixed, it is possible to modify the relative extension.

Exemplary radiation protection apparatus 10' also includes a drive mechanism 19, operatively connected to first (or/and second) radiation shield assembly 11 and control unit 18, and configured for extending or/and retracting a selected number of radiation shield segments 12 in accordance with variable extensions determined by control unit 18. Control unit 18 optionally determines contour of radiopaque screen edge 16 correlatively with or/and in response to analysis of the surface curvature of the object. In some embodiments, each of the radiation shield segments 12 is individually extendable or retractable relative to support base 14 or/and relative to one or more other radiation shield segments 12.

In some embodiments, a global power supply 20 may be used to power central parts of radiation protection apparatus 10', while each of the radiation shield segments 12 may be individually powered by a local power supply (20A, 20B, and 20C, for example). Each local power supply is configured for locally providing power for operating a separate unit or group of radiation shield segments 12 (12A, 12B and 12C, respectively, in this example). Optionally, control unit 18 optionally includes a plurality of controllers (18A, 18B, and 18C, for example), each is configured for controlling a single separate unit or group of the radiation shield segments 12 (12A, 12B and 12C, respectively, in this example). Optionally, drive mechanism 19 includes a plurality of drivers (19A, 19B, and 19C, for example), each is configured for extending or/and retracting a single separate unit or group of the radiation shield segments 12 (12A, 12B and 12C, respectively, in this example).

A data-information processing unit 21 may also be provided, being operatively connected to, and configured for processing data-information associated with, first (or/and second) radiation shield assembly 11 and control unit 18. Optionally, data-information processing unit 21 is configured for determining reactive actuation parameters of some of radiation shield segments in response to relative positioning of free end 17 of one or more others. The relative positioning of free end 17 may relate to a maximally or/and minimally allowable distance between free end 17 and the opposing portion of the object, or to a maximally allowable force measured when forcing free end 17 against the opposing portion of the object.

Control unit 18 may be configured for controlling reactive actuation of some radiation shield segments (e.g., radiation shield segments 12C) in response to relative positioning of at least one free end 17 of other radiation shield segments (e.g., free end 17A of radiation shield segment 12A). Optionally, extension of these some radiation shield segments (12C, in this example) changes, via the reactive actuation, in relation to a predetermined ratio of extension and extension of the at least one of the other radiation shield segments (12A, in this example). In some such embodiments, radiation shield segments 12C fully retract in response to this reactive actuation to extension of radiation shield segment 12A, for example.

Exemplary radiation protection apparatus 10' may also include an optical capturing device 22 configured to capture images of at least some of radiation shield segments 12 or/and of the object (e.g., subject 1). The captured images may include any type of information which facilitates or assists in building representation of the surrounding environment, including information from visible light or/and from non-visible light (including, for example, ultrasonic means). Optionally, alternatively or additionally, exemplary radiation protection apparatus 10' may further include a sensing unit (similar or identical to sensing unit 24 shown in FIG. 5, for example) that is operatively connected to at least one radiation shield assembly.

In some embodiments, at least one free end 17 is connected to a flexible spacer 23, optionally radiopaque to the radiation emitted by the X-ray system, optionally configured for spacing or/and compressing between the at least one free end 17 and relative to an opposing portion of the object, or/and to conform to a surface curvature of the object. In some embodiments, flexible spacer 23 is configured to move or/and deform in accordance with opposing body surface curvature it meets. The flexible spacer 23 may be fixed in a chosen angle relative to the radiation shield segment it is connected to, and may be aligned or nonaligned with, so it may deform in accordance with surface curvature in contact. Optionally and alternatively, flexible spacer 23 is configured to individually move relative to the free end 17 it is connected to, such as by way of bending, rotating, pivoting, and shifting away from alignment with the radiation shield segment 12 connected thereto. Flexible spacer 23 may be 'passive' in the sense that it is configured such that any individual relative movement thereof is facilitated in reaction to compressing against the object or/and conforming to the surface curvature of the object. Optionally and alternatively, flexible spacer 23 may be 'active' in the sense that it is configured to move according to a pre-calculated relative movement determined before contacting opposing boundary of the object.

Figure 5:
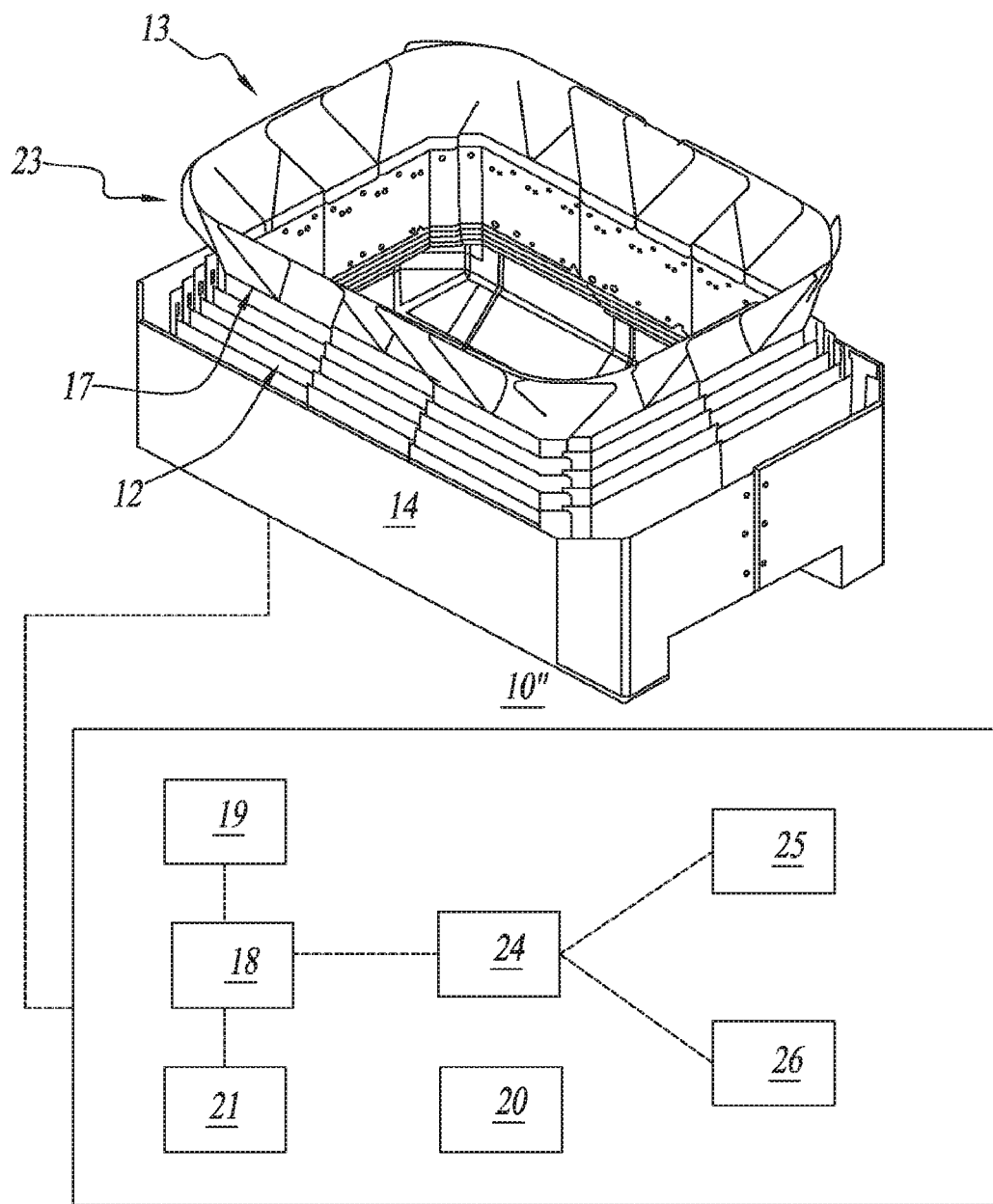

FIG. 5 schematically illustrates another exemplary embodiment of the radiation protection apparatus, and referenced as exemplary radiation protection apparatus 10", highlighting exemplary apparatus components and operative connects thereof. Exemplary radiation protection apparatus 10" corresponds to exemplary radiation protection apparatus 10 equipped with second radiation shield assembly 13 (although it may be equipped, also or instead, with first radiation shield assembly 11, for example). Exemplary radiation protection apparatus 10" includes a control unit 18, operatively connected to, and configured for controlling operation of, second (or/and first) radiation shield assembly 13, and at least one of radiation shield segments 12, thereby defining positioning of at least one of free ends 17 relative to an opposing portion of the object (e.g., subject 1).

In this exemplary embodiment shown in FIG. 5, control unit 18 is configured for globally controlling all separate units or groups of radiation shield segments 12. Optionally, control unit 18 determines variable extensions of radiation shield segments 12 according to the selected length of at least one of radiation shield segments 12. Each discrete radiation shield segment 12 is individually extendable or retractable from a location of support base 14. Control unit 18 optionally determines contour of radiopaque screen edge 16 correlatively with or/and in response to analysis of the surface curvature of the object. In some embodiments, each of the radiation shield segments 12 is individually extendable or retractable relative to support base 14 or/and relative to one or more other radiation shield segments 12.

Exemplary radiation protection apparatus 10" also includes a drive mechanism 19, operatively connected to second (or/and first) radiation shield assembly 13 and control unit 18, and configured for extending or/and retracting a selected number of radiation shield segments 12 in accordance with variable extensions determined by control unit 18. Optionally, in this exemplary embodiment, drive mechanism 19 is configured for globally extending or/and retracting all separate units or groups of radiation shield segments 12, if and when required (and prescribed by control unit 18). In some embodiments, a global power supply 20 may be used to power central parts of radiation protection apparatus 10", and optionally, in this exemplary embodiment, global power supply 20 is configured for globally providing power for operating all components of exemplary radiation protection apparatus 10", if and when required, and according to control by control unit 18.

A data-information processing unit 21 may also be provided, being operatively connected to, and configured for processing data-information associated with, second (or/and first) radiation shield assembly 13 and control unit 18. Optionally, data-information processing unit 21 is configured for determining reactive actuation parameters of some of radiation shield segments in response to relative positioning of free end 17 of one or more others. The relative positioning of free end 17 may relate to a maximally or/and minimally allowable distance between free end 17 and the opposing portion of the object, or to a maximally allowable force measured when forcing free end 17 against the opposing portion of the object.

In some embodiments, at least one free end 17 is connected to a flexible spacer 23, optionally radiopaque to the radiation emitted by the X-ray system, optionally configured for spacing or/and compressing between the at least one free end 17 and relative to an opposing portion of the object, or/and to conform to a surface curvature of the object. In some embodiments, flexible spacer 23 is configured to move or/and deform in accordance with opposing body surface curvature it meets. The flexible spacer 23 may be fixed in a chosen angle relative to the radiation shield segment it is connected to, and may be aligned or nonaligned with, so it may deform in accordance with surface curvature in contact. Optionally and alternatively, flexible spacer 23 is configured to individually move relative to the free end 17 it is connected to, such as by way of bending, rotating, pivoting, and shifting away from alignment with the radiation shield segment 12 connected thereto. Flexible spacer 23 may be 'passive' in the sense that it is configured such that any individual relative movement thereof is facilitated in reaction to compressing against the object or/and conforming to the surface curvature of the object. Optionally and alternatively, flexible spacer 23 may be 'active' in the sense that it is configured to move according to a pre-calculated relative movement determined before contacting opposing boundary of the object.

Exemplary radiation protection apparatus 10" may further include a sensing unit 24 that is operatively connected to at least one radiation shield assembly (in variation 10" to second radiation shield assembly 13, optionally also to first radiation shield assembly 11). In some embodiments, sensing unit includes at least one positioning sensor 25 coupled to at least one of radiation shield segments 12 and configured to sense and react to positioning or proximity of at least one free end 17 relative to opposing portion of the object, or to a contact therebetween. Optionally, alternatively or additionally, sensing unit 24 includes at least one radiation detecting sensor 26 configured to detect a portion of the radiation emitted by radiation source 8 (either directly or/and as scattered/residual radiation) and leaking through plurality of radiation shield segments 12. In some embodiments, sensing unit 24 is operatively connected to, and configured for providing data-information to, control unit 18. Optionally, control unit 18 is responsive to data-information provided by sensing unit 24. In some embodiments, exemplary radiation protection apparatus 10" may also include an optical capturing device (similar or identical to optical capturing device 22 shown in FIG. 4, for example) configured to capture images of at least some of radiation shield segments 12 or/and of the object (e.g., subject 1).

Figure 6A:
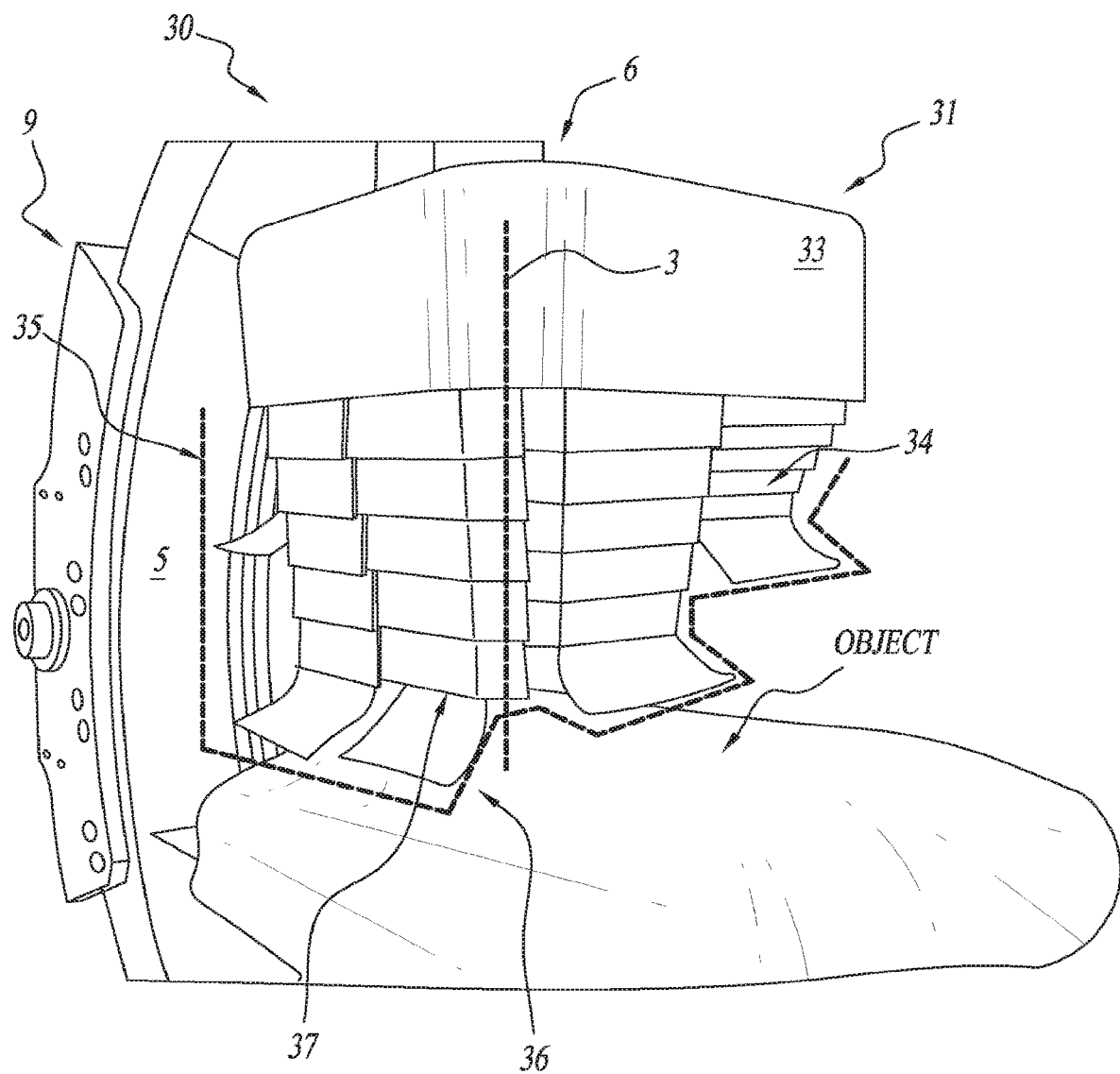
Figure 6B:
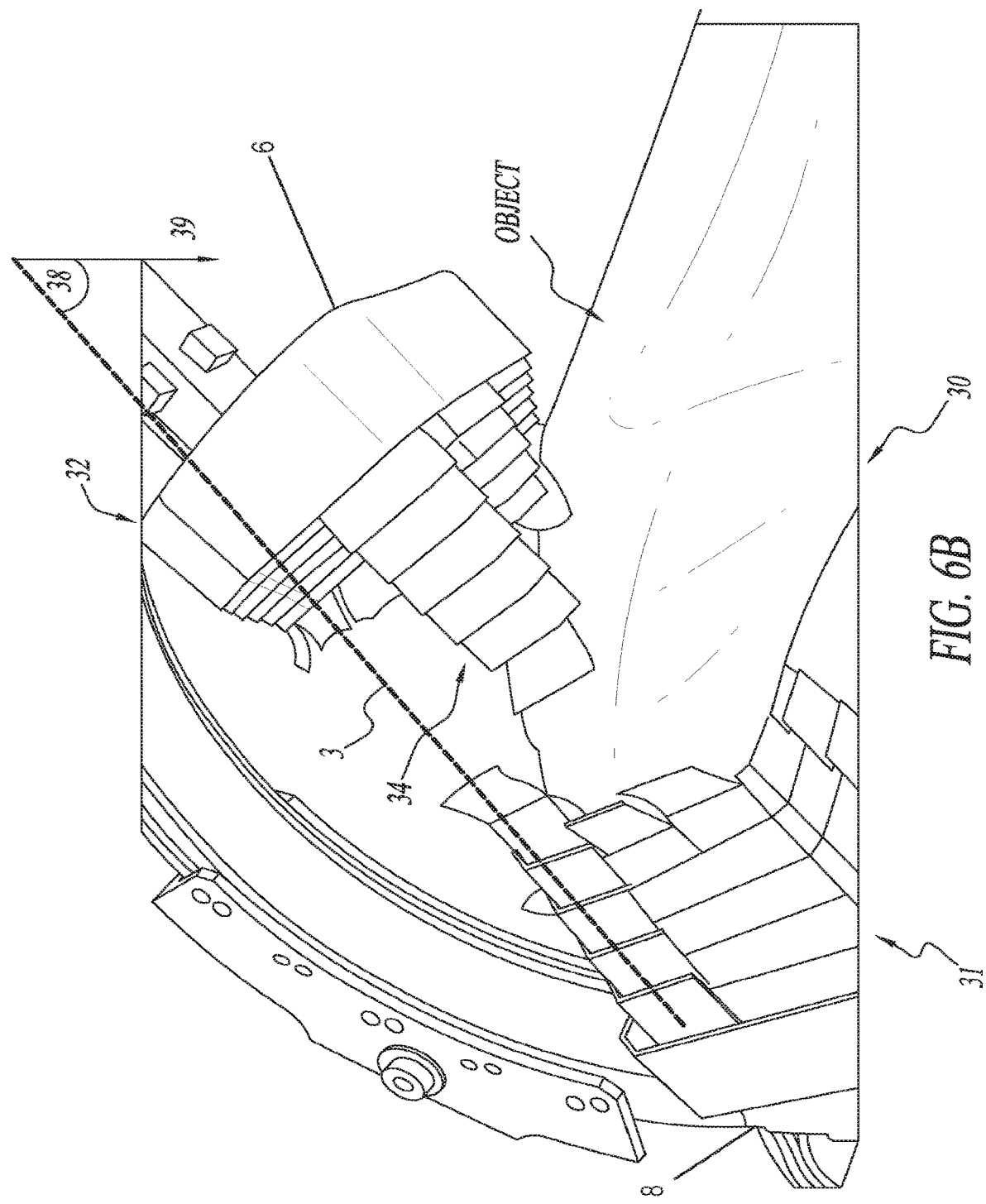
Figure 6C:
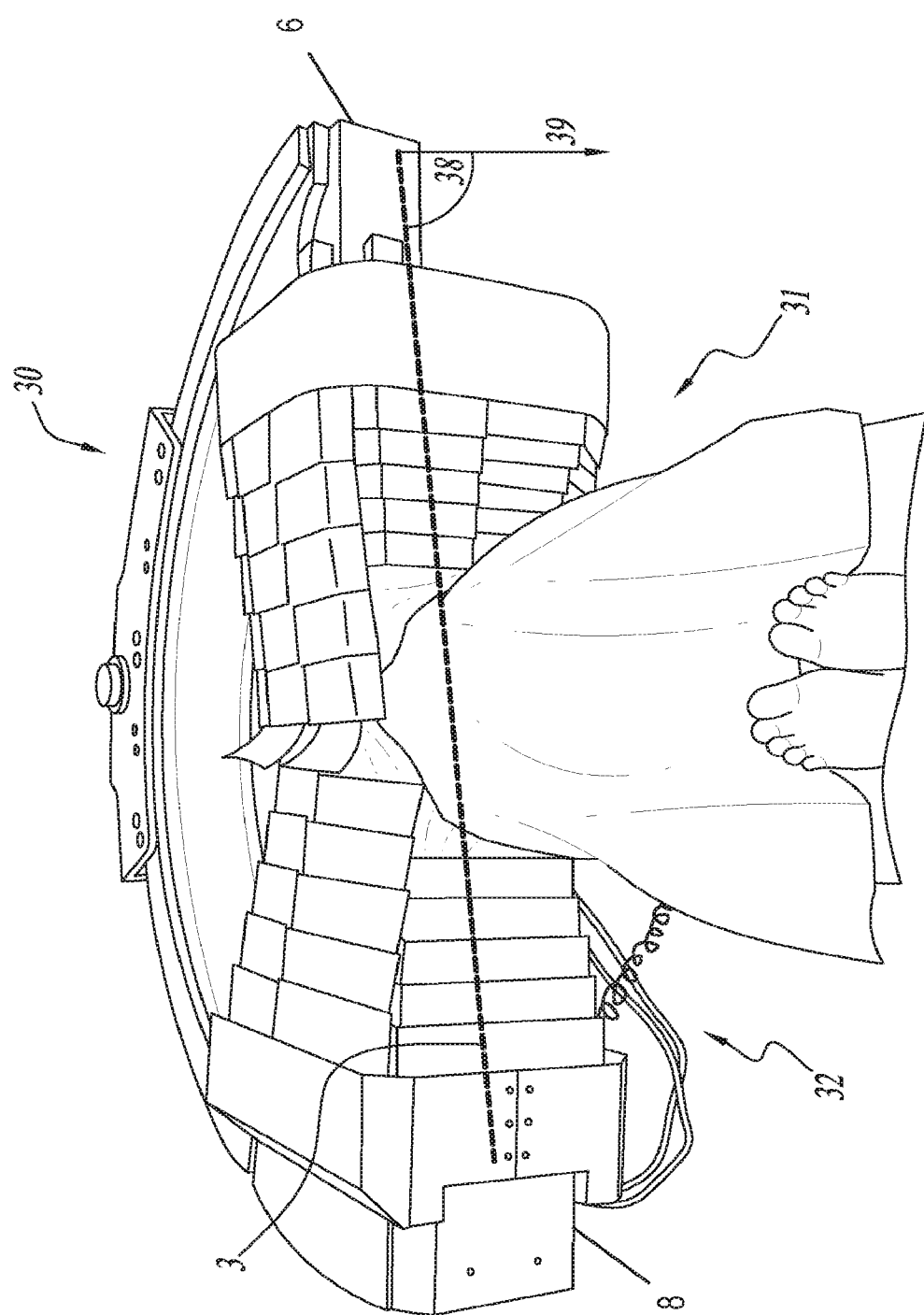

FIGS. 6A-6C schematically illustrate an exemplary radiation protection apparatus 30 positioned at different exemplary elevation angles. Exemplary radiation protection apparatus 30 may be identical or similar to herein illustratively described exemplary radiation protection apparatus 10 (FIG. 2), 10' (FIG. 4), or 10" (FIG. 5). In exemplary embodiments, exemplary radiation protection apparatus 30 is structurally and functionally configured to operate at different angles around the object, without loss of functionality.

As shown in FIGS. 6A-6C, exemplary radiation protection apparatus 30 is operatively connected to (for example, by being mounted on) an X-ray system similar to X-ray system 5 (shown in FIGS. 1 and 2) with a radiation source 8 and a radiation detector 6 positioned at opposing ends of C-arm 9. Exemplary radiation protection apparatus 30 includes a first radiation shield assembly 31 disposed in a region of space between radiation detector 6 and the object, and a second radiation shield assembly 32 disposed in a region of space between source 8 and the object. At least one radiation shield assembly (31 or/and 32) includes a first support base 33, operatively connectable to (and, for example, mountable around) radiation source 8, and a second support base 33 operatively connectable to (and, for example, mountable around) radiation detector 6. A plurality of radiation shield segments 34 are sequentially positioned relative to support base 33, thereby forming a contiguous radiopaque screen 35 configured for spanning at least partially around periphery of a region of interest, within the object, with a radiopaque screen edge 36 opposing the object. In some embodiments, at least one of the radiation shield segments 34 is individually, actively controllable to extend or contract to a selected length with a respective free end 37 thereof in a direction away from or towards support base 33, so as to locally change contour of radiopaque screen edge 36.

In exemplary embodiments, radiation source 8 and radiation detector 6 define beam axis 3 extending therebetween. Optionally, each of radiation shield segments 34 is configured to be structurally rigid so as to retain (up to) a maximally extended shape along an extension axis (which is substantially parallel to beam axis 3) that forms an exemplary elevation angle 38 relative to direction 39 of gravitational force ('gravity vector') acting upon the maximally extended shape. Optionally, alternatively or additionally, radiation shield segments 34 are angled relative to beam axis 3. Exemplary elevation angle 38 may be, for example, 15 degrees or more, optionally, particularly 30 degrees or more, optionally particularly 45 degrees or more, or optionally particularly 90 degrees or more.

FIG. 6A illustrates an example where the beam axis 3 is oriented substantially vertically. In different embodiments, and as shown in FIGS. 6B and 6C, for example, the orientation of beam axis 3 is modifiable, for example, by motion of C-arm 9 in different spatial angles, or, for example, by motion of the radiation source 8 relative to the radiation detector 6. FIG. 6B illustrates exemplary elevation angle 38 of about 45 degrees relative to the vertical gravity vector 39. FIG. 6C illustrates exemplary elevation angle 38 of nearly 90 degrees relative to the vertical gravity vector 39.

In some embodiments, the orientation of beam axis 3 is modifiable. In exemplary embodiments of radiation shield assembly 31 or/and 32, structural rigidity for each given radiation shield segment 34, or for a group of such radiation shield segments 34, is sufficient to retain the shape of each radiation shield segment throughout an exemplary elevation angle range of at least D degrees. In exemplary embodiments, D has a value of at least 10 degrees, or at least 15 degrees, or at least 20 degrees, or at least 25 degrees, or at least 30 degrees, or at least 45 degrees, or at least 60 degrees.

In some embodiments, by having sufficient rigidity for each radiation shield segment to retain its shape this prevents or mitigated shape-deformations which may block the image beam. In some embodiments, the term 'structural rigidity' refers to how each radiation shield segment is constructed—i.e. design, material, geometry (e.g. thickness), for example. In contrast, any other type of radiation shield constructed from highly flexible radiation shield segments, for example, the shield segments could 'bend' or sag under its own weight.

An aspect of some embodiments of the invention is a method of shielding surroundings from radiation emitted by an X-ray system externally positioned around the periphery of a region of interest located inside an object.

FIG. 7A is a flow diagram of an exemplary embodiment (indicated as, and referred to by, reference number 50), including the indicated exemplary steps (procedures/processes) thereof, of such a method 50 of shielding surroundings from electromagnetic emitted by an X-ray system, such as X-ray system 5 (or X-ray system 30). Herein, the exemplary embodiment 50 of a method of shielding surroundings from radiation emitted by an X-ray system externally positioned around the periphery of a region of interest located inside an object is also referred to as the radiation shielding method. The exemplary embodiment 50 of the radiation shielding method presented in FIG. 7A, in a non-limiting manner, is implementable using various types of X-ray systems, such as exemplary X-ray system 5 (FIG. 1), or exemplary X-ray system 30 (FIGS. 6A-6C). Similarly, various types of X-ray systems, such as exemplary X-ray system 5 (FIG. 1), or exemplary X-ray system 30 (FIGS. 6A-6C), in a non-limiting manner, are usable for implementing exemplary embodiments of the radiation shielding method, such as exemplary embodiment 50 of the radiation shielding method presented in FIG. 7A.

As shown in FIG. 7A, in a non-limiting manner, and in some embodiments, such as exemplary embodiment 50, the radiation shielding method includes the following exemplary steps (procedures/processes).

In 52, there is providing at least one radiation shield assembly connectable to the X-ray system. The radiation shield assembly includes a support base operatively connectable to (and, for example, mountable around) a radiation source or a radiation detector of the X-ray system. The radiation shield assembly also includes a plurality of individually controllable radiation shield segments sequentially positioned relative to (for example, around) the support base and extendable towards the object.

In 54, there is determining a chosen proximity of a free end of at least one of the radiation shield segments to an opposing portion of the object. Chosen proximity may also include 'zero' proximity, which means direct contact with the object, optionally at a chosen magnitude of force within an acceptable range of forces, applied or developed therebetween.

In 56, there is individually actuating, and extending or retracting one or more of the at least one radiation shield segments relative to the support base, until the free end is at the chosen proximity (including 'zero' proximity) to the opposing portion of the object.

In exemplary embodiments, such as in exemplary embodiment 50, the radiation shielding method additionally includes one or more of the following exemplary steps (procedures). The following exemplary steps (procedures) may be performed prior to, during, or/and after, performing any of steps (procedures) 52, 54, and 56. In exemplary embodiments, all of the following exemplary steps (procedures) are performed before (i.e., prior to) performing step (procedure) 52 of exemplary embodiment 50 of the radiation shielding method.

Setting up and preliminary testing of the X-ray system 5 and any of its components, including but not limited to radiation source 8 and radiation detector 6.

Defining the region of interest 4 within the object (subject 1) and its periphery, so that the X-ray system 5 can effectively image (or treat) a target anatomic location or organ within the periphery and across the area defining that region of interest 4.

Marking chosen margins radially away from the region of interest 4 periphery, above or around which the radiopaque screen 15, formable by radiation protection apparatus 10', can be later mounted.

Positioning the object (subject 1) for effectively utilizing the X-ray system (on top of bed 7), in a manner by which the radiation protection apparatus 10' can be applied to shield surroundings from around the region of interest 4 periphery, optionally above or around the marked margins allocated thereto.

Connecting (e.g., by way of mounting) or verifying connection of first and second radiation shield assemblies 13 and 11 to X-ray system 5, by which support base 14 of each of the radiation shield assemblies is operatively connected to (for example, and positioned around) radiation source 8 and radiation detector 6, respectively, and that the plurality of individually controllable radiation shield segments 12 are sequentially positioned relative to each support base 14 and extendable towards the object (subject 1).

In exemplary embodiments, such as in exemplary embodiment 50, the radiation shielding method may further include at least one of the followings steps (procedures), not necessarily in the following order.

Determining a chosen proximity of free end 17 of at least one of the radiation shield segments 12 to an opposing portion of the object. Determining the chosen proximity (including 'zero' proximity) may be performed by using at least one positioning sensor 25 configured for detecting positioning of at least one of radiation shield segments 12 relative to the object. The determining may be performed by using a data-information processing unit 21.

Individually actuating one or more of radiation shield segments 12 relative to respective support base 14, until that free end 17 is at the chosen proximity to the opposing portion of the object. The individually actuating may be performed by using drive mechanism for extending or/and retracting a selected number of the radiation shield segments 12 in correlation to the detected position.

Optionally, repeating the determining or/and the individual actuating of that at least one radiation shield segments 12, or/and of one or more others radiation shield segments 12, until collectively forming a contiguous radiopaque screen 15 spanning at least partially around the periphery of the region of interest 4 with an edge 16 contoured correlatively with a surface curvature of the object.

Using at least one radiation detecting sensor 26 for detecting leakage of portion of the radiation emitted by radiation source 8 through the contiguous radiopaque screen 15, and optionally controlling the drive mechanism in accordance with results of the radiation detecting.

Programming or applying one or more pre-sets readily programmed in radiation protection apparatus 10' or/and X-ray system 5 which optionally limits automatic or/and bounded activity of at least one radiation shield segment 12, or/and an interrelated sequence of some or all radiation shield segments 12.

A first exemplary pre-set may include recognition of a particular anatomic location or organ (e.g., head of subject 1 or hands of any of the medical personnel), or of certain artifacts (e.g., medical apparatuses or tools), which will affect limited extension or full retraction of one or more radiation shield segments 12 in order to avoid contact or collision, or prevent undesired shielding or motion in its premises, for example.

A second preliminary pre-set may include certain covering schemes of particular sectors around region of interest periphery, so, for example, one scheme may include full or partial extension of several sequential radiation shield segments 12 thereby forming contiguous radiopaque screen 15 spanning less than 360 degrees (optionally 180 degrees or less, or optionally 90 degrees or less) around the region of interest 4 periphery (one example is shown in FIG. 4, where first radiation shield segment 12A is fully extended, and adjacent second radiation shield segment 12B is partially extended, while other (optionally, rest) of the radiation shield segments 12C are fully retracted. Another exemplary scheme may include one or more (adjacent or remote) radiation shield segment 12 be substantially or fully retracted, among fully (including substantially) extended other radiation shield segments 12, with free ends 17 thereof approximating body of object, in order that medical personnel can reach the region of interest directly via these formed gaps.

A third preliminary pre-set may include prescribed partial (moderate or substantial) or full retraction of one or more (e.g., all) radiation shield segments 12 upon or during shift of C-arm 9, radiation detector 6, radiation source 8, or/and bed 7, for example, relative to the object (subject 1 or particularly region of interest 4). One such pre-set, for example, may dictate full retraction of some or all radiation shied segments 12 during substantial shift (for example, repositioning of C-arm 9 relative to subject 1). Another such pre-set, for example, also known as "hover mode", may dictate moderate retraction (relative or fixed) of some or all radiation shield segments 12 during slight repositioning of bed 7 relative to radiation source 8, for example.

Figure 7B:
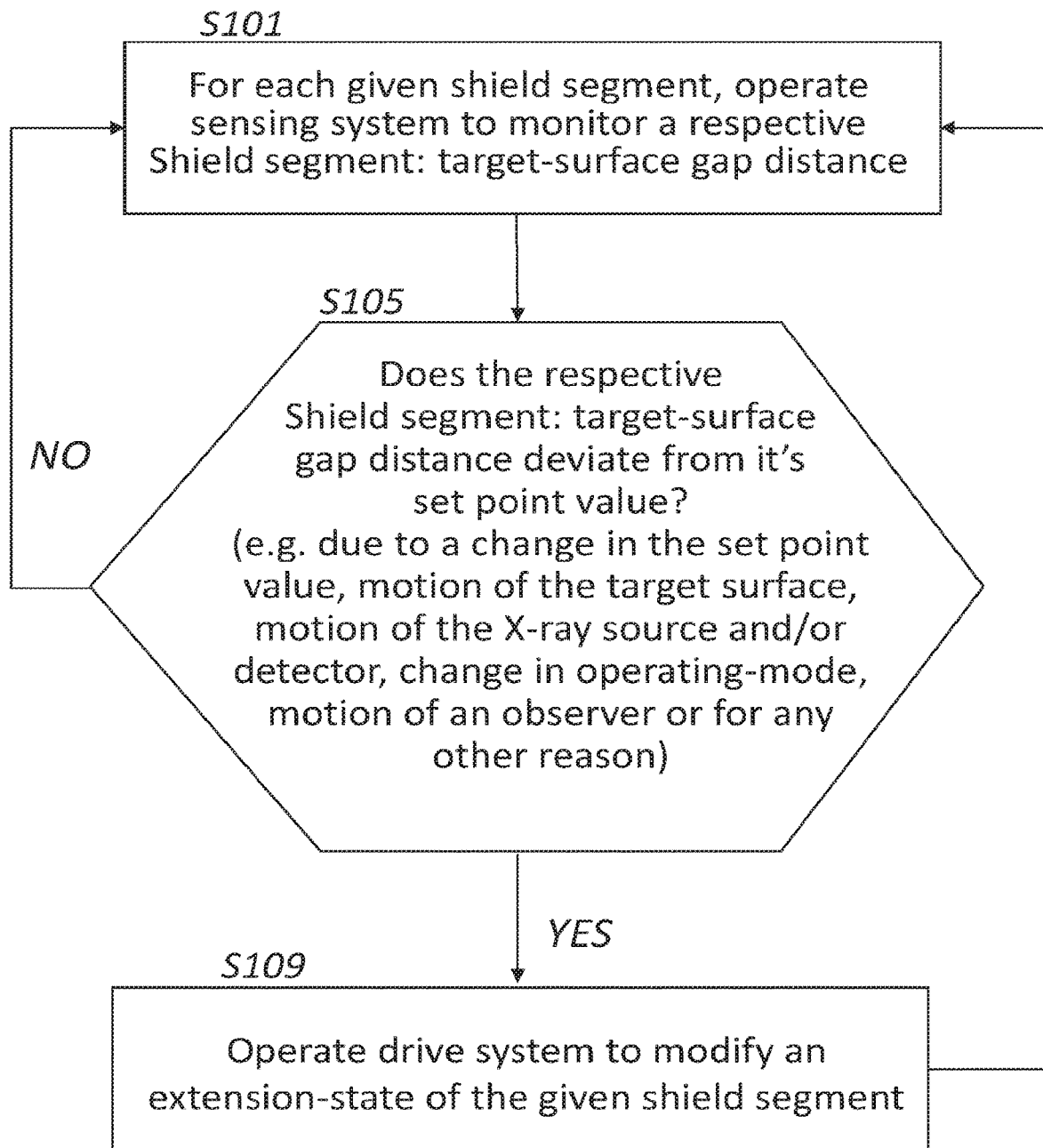
FIG. 7B is a flow chart of an exemplary routine (process) for a shield in 'hover mode' to regulate a gap distance between a distal end of radiation shield segments and a target or opposing surface, according to some embodiments of the invention.

FIG. 7B is a flow chart of an exemplary routine (process) for a shield in 'hover mode' to regulate a gap distance between a distal end of radiation shield segments and a target or opposing surface may be regulated to a non-zero set-point value.

In exemplary step (procedure) S101, for each given radiation shield segment, a sensing system is operated to monitor a respective non-zero radiation shield segment: target surface gap-distance. A common sensing system may sense the distances for multiple radiation shield segments or/and each radiation shield segment may be associated with its own respective segment-specific sensing system.

In exemplary step (procedure) S105, for each radiation shield segment it is determined (e.g. by electronic circuitry—for example, software executing on a digital computer) if the respective gap-distance deviates from it's set-point value. This may be due to a number of causes (or combinations of causes) including but not limited to: (i) a change in the setpoint value (e.g. the user may wish to cause the shield to 'hover at a greater distance' or 'lesser distance' and may input this information via a Graphical User Interface (GUI)); (ii) motion of the opposing or target surface, motion of radiation source 8 or/and detector 6; (iii) motion of an 'observer' (e.g. a person in the room); (iv) rotation of the C-arm; (v) Table adjustment and (iv) a change in an operating mode.

In one example related to 'motion of an observer' there may be a single person in the room other than subject 1—e.g. only one medical member (physician) in the room. In one example, the physician may stand on one side of the table or another. In another example, there may be a need to provide absolute 360 degrees shielding (e.g. contact between the radiation shield segments and the opposing surface or a 'small gap distance') only for the side of the table where the physician is located—for patient comfort, radiation shield segments on the other side of the table may be operated in 'hover mode' at a larger gap distance. In this example, when the physician walks from one side of the table to the other, the radiation shield (i.e. according to input from sensor system and actuating by the drive mechanism) detects this and responds by: (i) reducing the gap distance (or even leaving hover mode to the radiation shield segments contact subject 1) on the side of the table to which the physician is walking; and (ii) increasing the gap distance on the side of the table to which the physician is leaving.

In exemplary step (procedure) S109, in response to a detected deviation between respective gap-distance for a given radiation shield segment (e.g. as detected by the detection system) the drive mechanism modifies an extension state of one or more radiation shield segments to reduce or eliminate, for each given radiation shield segment, a respective deviation between (A) the respective measured gap distance between a location on the given radiation shield segment and the opposing surface and (ii) a respective set-point gap distance for the given radiation shield segment. Thus, if the deviation as measured in steps (procedures) S101-S105 is 'positive' (i.e., the gap distance exceeds its set-point value), the drive mechanism would operate to reduce the gap distance to reduce or eliminate the deviation—i.e. by increasing an extension state of a radiation shield segment to move location(s) on the radiation shield segment towards the opposing surface. If the deviation as measured in steps (procedures) S101-S105 is 'negative' (i.e., the gap distance is less than its set-point value), the drive mechanism would operate to increase the gap distance to reduce or eliminate the deviation—i.e. by decreasing an extension state of a radiation shield segment to move location(s) on the radiation shield segment away the opposing surface.

Thus, FIG. 7B is a flow chart describing a method (process) of regulating radiation shield segment-specific gap distances to a common set-point value or to a different set-point values where each radiation shield segment is regulated to a different set-point value. This is performed according to measured distances, i.e., either via direct distance measurement or via measurement of an 'indication' of distance between a location on the radiation shield segment and the opposing surface.

The 'opposing surface' may be a common 'target' surface for multiple radiation shield segments or each radiation shield segment may be associated with a different respective opposing/target surface.

Some embodiments of the invention relate to a radiation protection apparatus for an X-ray system that includes an X-ray source and detector defining a beam axis therebetween. In exemplary embodiments, the radiation protection apparatus includes a first radiation shield assembly having a support base located at one end of the beam axis. In exemplary embodiments, the first radiation shield assembly includes a first plurality of (X-ray opaque) radiation shielding segments disposed at different locations around the beam axis to collectively form an X-ray opaque screen, wherein each of the radiation shielding segments is individually extendable from and retractable towards the support base location along the beam axis, to provide a hovering mode according to the following technical features and characteristics.

In exemplary embodiments, the radiation protection apparatus further includes a sensing unit configured to sense a respective proximity between a respective point on each radiation shielding segment and a respective target surface. In exemplary embodiments, the radiation protection apparatus further includes a controller configured to receive proximity data from the sensing unit. In exemplary embodiments, the radiation protection apparatus further includes a drive mechanism configured for extending or/and retracting radiation shielding segments of the plurality of radiation shielding segments in response to output of the controller. In exemplary embodiments, the controller operates the drive mechanism in accordance with the proximity data received from the sensing unit so as to extend or/and retract the segments. In exemplary embodiments, for each given radiation shielding segment, the controller is configured to regulate a gap distance between (i) a respective point of the given segment and (ii) a respective target surface, to a respective pre-determined value.

FIGS. 8A-8B schematically illustrate side views of an exemplary (discrete) radiation shield segment 100 of an exemplary radiation protection apparatus which may be similar in function or/and structure to radiation protection apparatus 10, 10', 10", or 30, for an X-ray system, such as X-ray system 5. In exemplary embodiments, radiation shield segment 100 includes a radiopaque cover member 101 which may be configured to prevent from passing there-across (e.g., across thickness thereof) over 10%, optionally over 25%, optionally over 50%, optionally over 75%, or optionally over 90%, of radiation flux originating from the X-ray system. In some embodiments, radiopaque cover member 101 is substantially flexible so it can bend, curve or/and be rolled (such as in/around a drum).

In exemplary embodiments, radiation shielding segment 100 further includes a length dispenser 102 mountable on the X-ray system to cover a particular sector around a radiation source (e.g., radiation source 8) or radiation detector (e.g., radiation detector 6) of the X-ray system. In some embodiments, dispenser 102 is configured for changing or/and maintaining a deployed length 103 of cover member 101 between dispenser 102 and a free end 104 of cover member 101 (from within a range of deployed lengths). Cover member 101 is optionally arranged (as shown) in a form of a roller-shade, such that a remaining non-deployed length thereof is rolled in dispenser 102.

In exemplary embodiments, radiation shield segment 100 may further include a (laterally rigid) first frame member 106 that is connected with a first end 107 thereof to dispenser 102, and connected with a second end 108 thereof to cover member free end 104. In some embodiments, first frame member 106 is extendible or contractible (between a fully expanded form as indicated in FIG. 8A and a fully retracted form as indicated in FIG. 8B) to allow spanning of the deployed length 103 (or any deployed length from within the range of deployed lengths), while maintaining structural rigidity sufficient to support cover member 101 in a lateral straighten form along its deployed length 103. First frame member 106 optionally includes a plurality of first frame sections 106i telescopically arranged and slidable inside one another. First frame member 106 may be extended or extendable along the deployed length 103 (or any deployed length from within the range of deployed lengths) thereby covering a first (lateral) side 110 of cover member 101.

In exemplary embodiments, radiation shield segment 100 may include a (laterally rigid) second frame member 111 being extendible or collapsible to allow deployed length 103 from (or any deployed length from within the range of deployed lengths). Second frame member 111 may be extended or extendable along the deployed length 103 above a second (lateral) side 112 of cover member 101, opposing first side 110 thereof. Second frame member 111 optionally includes a plurality of second frame sections 111i telescopically arranged and slidable inside one another.

In exemplary embodiments, radiation shielding segment 100 further includes a controller 105 that is operatively linked to length dispenser 102 and is configured to actuate dispenser 102 or/and to control extent of the deployed length 103, according to a selected extent.

In exemplary embodiments, radiation shield segment 100 further includes an actuator 109 that is configured to force cover member 101 or/and first frame member 106 or/and second frame member 111 to extend or contract when shifting from deployed length 103 within the range of deployed lengths. In some embodiments, actuator 109 is configured to act against a continuous pulling force (for example, generated by a returning spring acting on the drum, the frame or/and the cover member), thereby forcing together the flexible cover member into a substantially spatial straight form (to avoid sagging, for example). Actuator 109 is operatively connected to a contact sensor 113 configured to indicate a magnitude of force or/and pressure developing or affecting shielding segment 100 or members thereof. Optionally, alternatively or additionally, actuator is operatively connected to a proximity sensor 114 configured to indicate a distance from a motion resisting object, which may be a bed, a body part of a subject (human or animal patient, for example), as indicated in FIG. 2, or others.

In exemplary embodiments, radiation shield segment 100 further includes a flexible radiopaque spacing member 116 that is connected to cover member free end 104, and is configured for spacing or/and compressing between cover member free end 104 and a motion resisting object. Optionally, alternatively or additionally, spacing member 116 is configured to conform to shaped surface of the motion resisting object. In an exemplary embodiment, the spacing member is in a form of a flap, such that each radiation shield segment has a respective flexible or/and individually deployable flap attached to a distal end thereof. For example, deploying the segment to a target surface (e.g. the subject being imaged or/and the table) may entail multistage operation—after the radiation shield segment is in place (i.e. at its proper multi-extension state) the flap may be deployed to the target surface—e.g. so that a flat surface of the flap is flush against the target surface.

FIGS. 9A-9B schematically illustrate top views of an exemplary (discrete) radiation shield segment 100, and an exemplary assembly of such (discrete) radiation shield segments, respectively. As shown in FIG. 9B, a number of radiation shield segments 100 are interconnected to form an encircling coverage which can be part of the radiation protection apparatus provided around a radiation source or/and a radiation detector of the X-ray system. Each pair of radiation shield segments 100 (e.g., a first 100a and a second 100b radiation shield segments 100) are juxtapositionally arranged (horizontally or vertically, or in any angle). First radiation shield segment 100a is equipped with a first cover member 101a supported with first frame member 106 along a first adjacent side 110a thereof. Second radiation shield segment 100b is equipped with a second cover member 101b supported with second frame member 111 along a second adjacent side 112b thereof. First radiation shield segment adjacent side 110a lies adjacent to second radiation shield segment adjacent side 112b, as shown.

As shown, first frame member 106 includes a lateral extension 117 sized for covering a seam (or a gap) 118 between first radiation shield segment adjacent side 110a and second radiation shield segment adjacent side 112b and for covering second radiation shield segment adjacent side 112b. Second frame member 111 is sized and shaped for mating against lateral extension 117 of adjacent first frame member 106.

Each discrete radiation shield segment may include interconnection means at both sides thereof which are configured to prevent lateral or sideways relative movement but to allow longitudinal or up-and-down relative movement, of each discrete radiation shield segment relative to all other radiation shield segments. As shown, each discrete radiation shield element 100 includes a number of carriers 119, each is part of or fixated via a stem 120 to a corresponding second frame section 111i. Each carrier 119 is sized and shaped for sliding in a track facilitated by a rail 121 (e.g. in a form of a cavity) being part of or connected to first frame member 106. Carriers 119, stems 120 and rail 121 are shaped, sized and configured not to interfere with the ability of the frame members to extend or contract within defined limits, as demonstrated for example in FIGS. 8A-8B.

An aspect of some embodiments of the invention is provision of an X-ray system including: a radiation source configured to emit radiation that is transmitted through an object and towards a radiation detector; and at least one radiation shield assembly including: a support base operatively connected to the radiation source or/and the radiation detector, and a plurality of individual radiation shield segments sequentially positioned relative to the support base. In such exemplary embodiments, each of the radiation shield segments is controllably, variably extendable or retractable between the radiation source or/and the radiation detector and the object. In such exemplary embodiments of an X-ray system, the plurality of radiation shield segments is configured for forming a contiguous radiopaque screen spanning at least partially around the X-ray system.

FIGS. 10A-10H schematically illustrate an exemplary X-ray system 250 to which is operatively connected (and mounted) an exemplary radiation protection apparatus 260 including a plurality of exemplary discrete radiation shield segments 200 having a radiopaque cover member in a form of a roller-shade, and assemblies thereof. X-ray system 250 may be similar in function or/and structure to X-ray system 5, and include a radiation source 251 and radiation detector 252 at both ends of a C-arm 253, capable of shifting in between different angles and positions relative to a bed 254. A subject (patient) 255, being the object of the X-ray system, can lay on bed 254, and C-arm 253 be so positioned, such that a region of interest 256 is provided in between radiation source 251 and radiation detector 252.

Radiation protection apparatus 260 may be similar in function or/and structure to any of radiation protection apparatus 10 and radiation protection apparatus 30, and include a first radiation shield assembly 262 disposed in a region of space between radiation detector 252 and table 254, and a second radiation shield assembly 251 disposed in a region of space between radiation source 261 and table 254. Nevertheless, only a single radiation shield assembly may be used as part of radiation protection apparatus 260, for example only in the region next to radiation source 251.

Figure 10A:
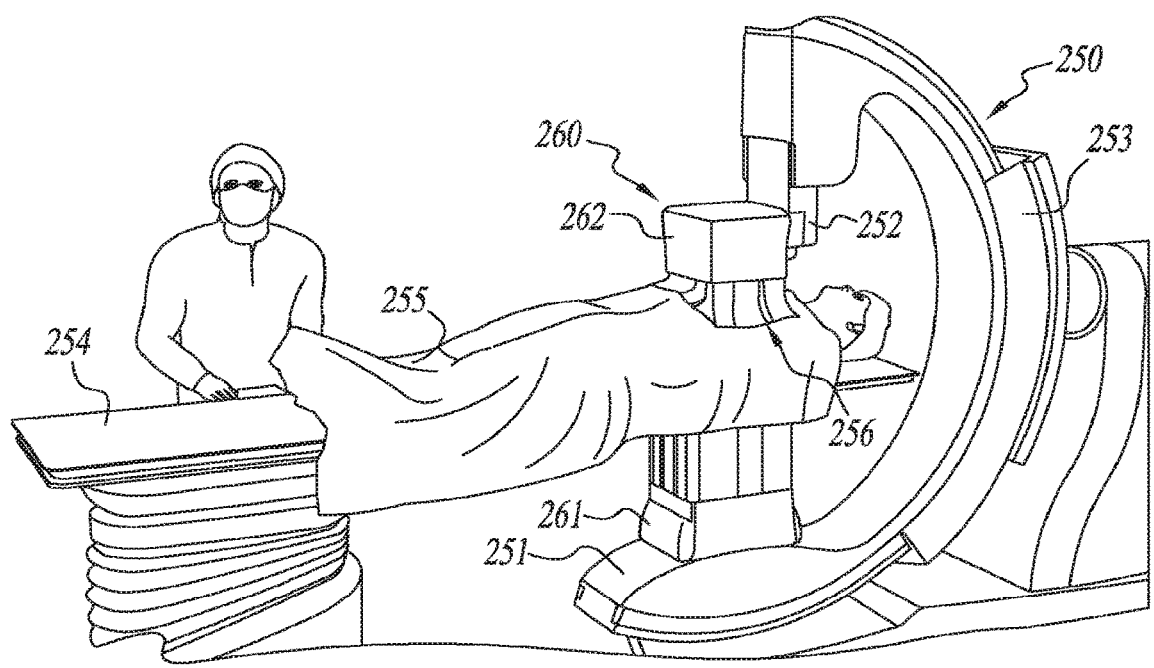
Figure 10B:
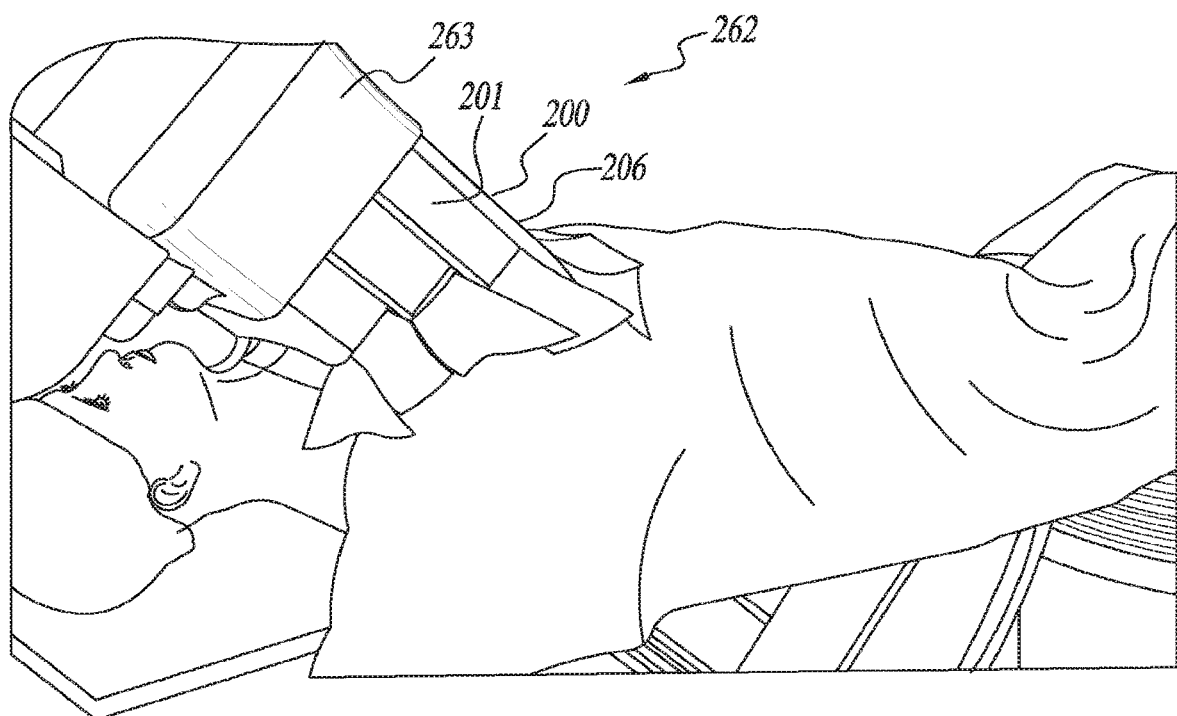

At least one radiation shield assembly (261 or/and 262) includes a support base 263 operatively connectable to radiation source 252 or radiation detector 251 of X-ray system 250. Support base 263 is optionally circumferential and rectangular, as shown in FIG. 10B, although it may capture only one side or sector around radiation source 251 or radiation detector 252 and be in a different form, such as of ellipse, circle, or a different form of tetragon.

A plurality of radiation shield segments 200 are sequentially positioned relative to support base 263, thereby forming a contiguous radiopaque screen configured for spanning at least partially around the periphery or region of interest 256, with a radiopaque screen edge opposing the object (subject 255). Any of radiation shield assemblies 261 and 262 can include any number of radiation shield segments 200 at any of its faces (sides) and in total. FIG. 10B shows radiation shield assembly 262 with three radiation shield segments 200 at each face, while FIG. 10F illustrates another variation of radiation shield assembly 262 with four radiation shield segments 200 at each face.

In some embodiments, at least one of the radiation shield segments 200 is individually, actively controllable to extend or contract to a selected length with a respective free end thereof in a direction away from or towards support base 263. In some embodiments, the radiation shield segments 200 are extendible or contractible longitudinally.

In exemplary embodiments, radiation shield segment 200 includes a radiopaque cover member 201 which may be similar in function or/and structure to radiopaque cover member 101 (showing only its deployed length section, for demonstrative purposes). In some embodiments, radiopaque cover member 201 is substantially flexible so it can bend, curve or/and be rolled (such as in a drum). Radiopaque cover member 201 may be dispensed or deployed via a dispenser 202 or by other means mountable on the X-ray system to cover a particular sector around an X-ray source or detector of the X-ray system. The dispenser may be controlled by use of a controller, and actuated by use of an actuator, as previously described. Cover member 201 is optionally arranged in a form of a roller-shade, such that a remaining non-deployed length thereof is rolled in drum provided with dispenser 202, for example.

In exemplary embodiments, discrete radiation shield segment 200 includes a first frame member 206 which is extendible or contractible in accordance with selected deployed length of the cover member 201. First frame member 206 includes a plurality of first frame sections 206i telescopically arranged and slidable inside one another. First frame member 206 covers both sides of a first side 210 of cover member 201, allowing sliding motion thereof relative to frame section 206i excluding the final (most inner) section which is connected to a free end 204 of cover member 201.

In exemplary embodiments, discrete radiation shield segment 200 includes a second frame member 211 being extendible or collapsible together with first frame member 206, above a second side 212 of cover member 201. Second frame member 211 includes a plurality of second frame sections 211i telescopically arranged and slidable inside one another. Second frame member 211 may be shaped and sized to mate geometrically with a recess 203 (as shown for example in FIG. 10D) provided along first frame member 206 in order to allow integration between adjacent discrete shielding segments while covering gaps or/and seams therebetween, using both frame members (for example, as shown in FIG. 10H).

Figure 10C:
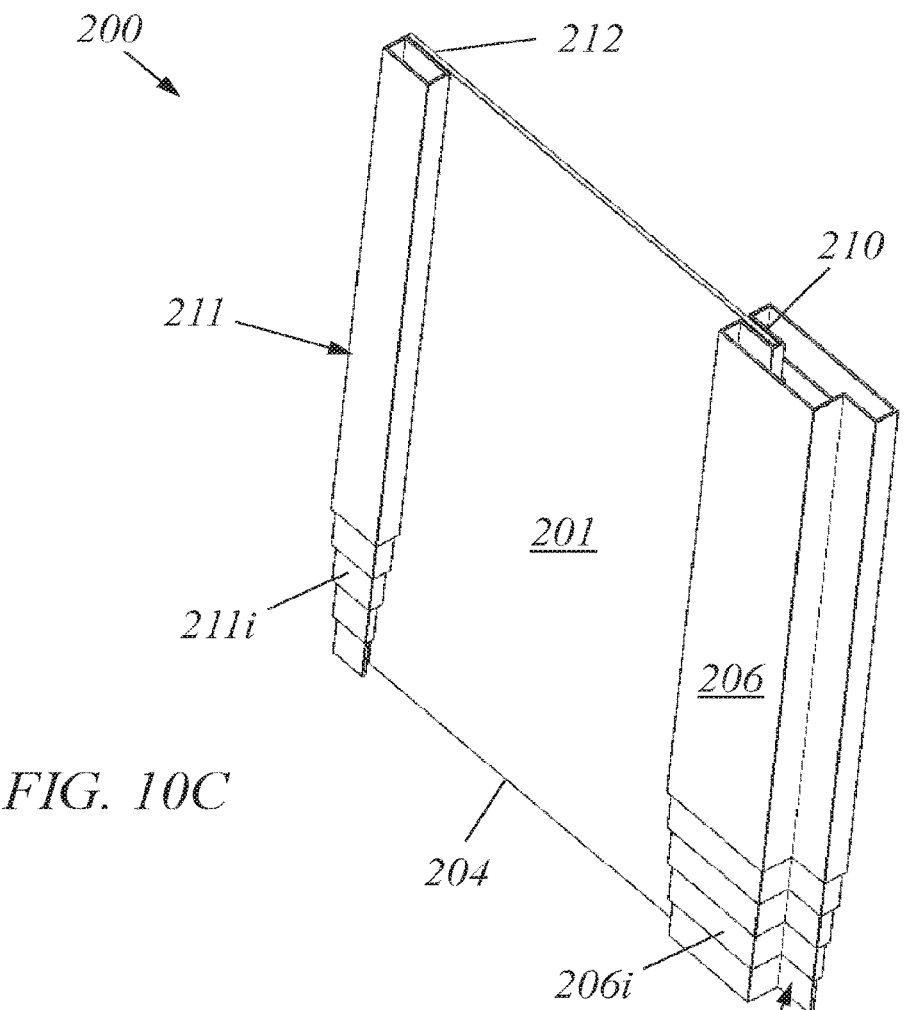
Figure 10D:
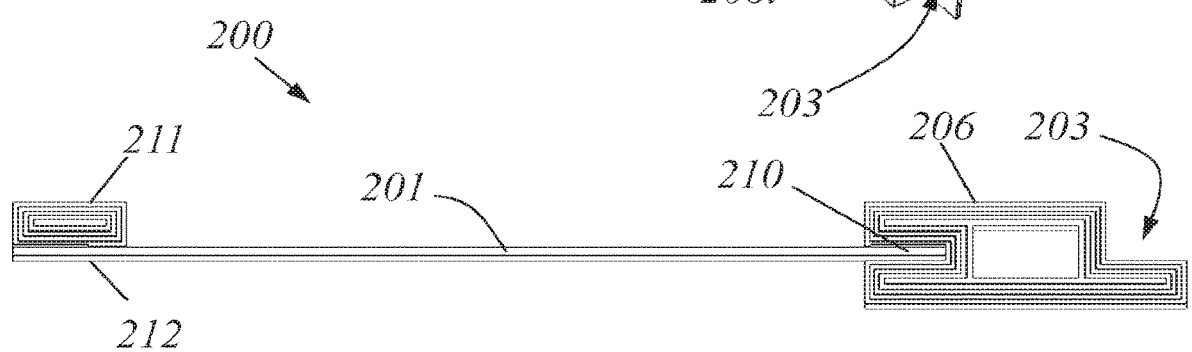
Figure 10E:
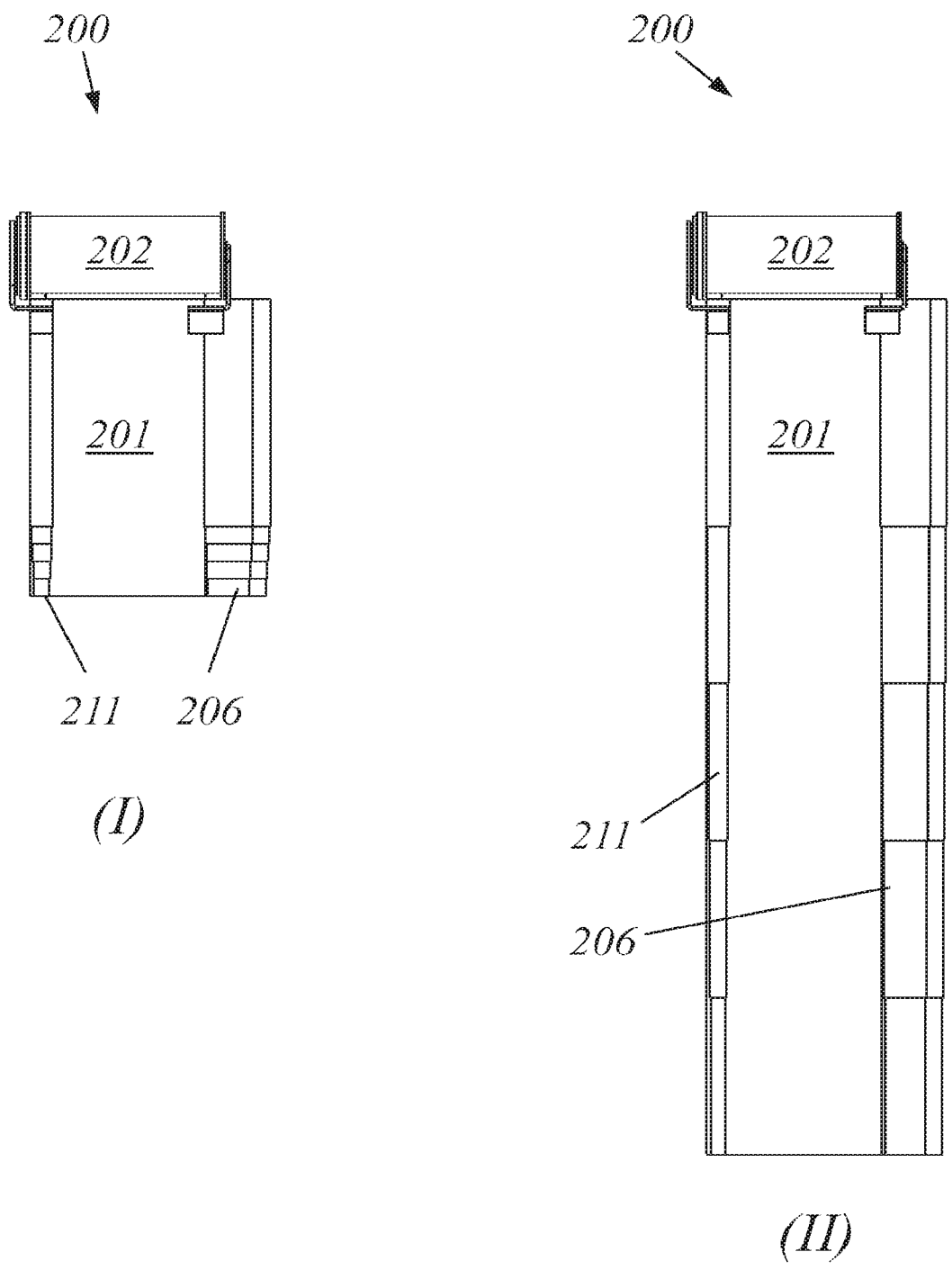
Figure 10F:
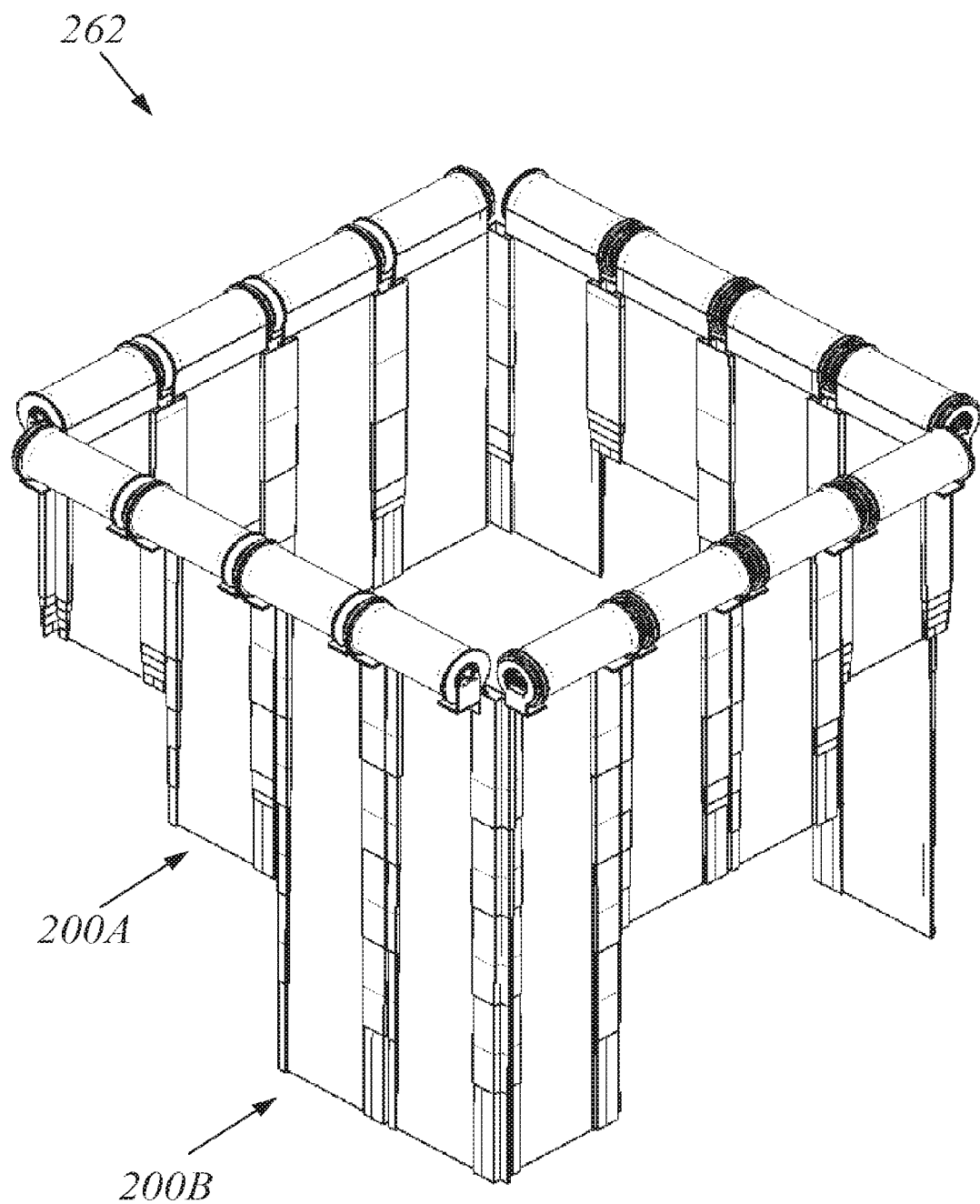

FIG. 10D shows a top view of exemplary discrete radiation shield segment 200 portion shown in FIG. 10C, presenting the concentric arrangement of all first and second frame sections. FIG. 10E(I) shows radiation shield segment 200 fully compacted while FIG. 10E(II) shows radiation shield segment 200 fully extended, together with cover member 201, first frame member 206 and second frame member 211.

Figure 10G:
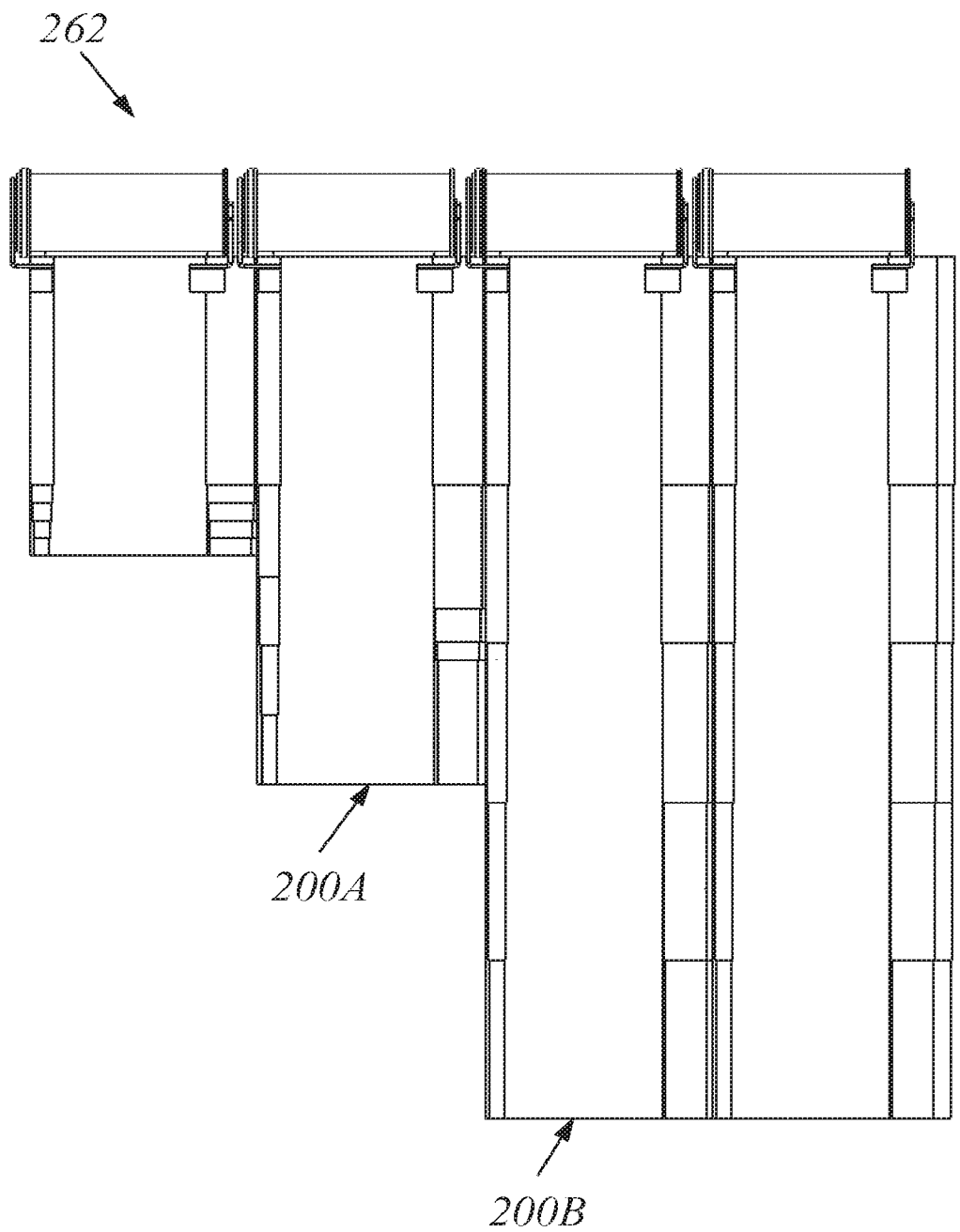
Figure 10H:
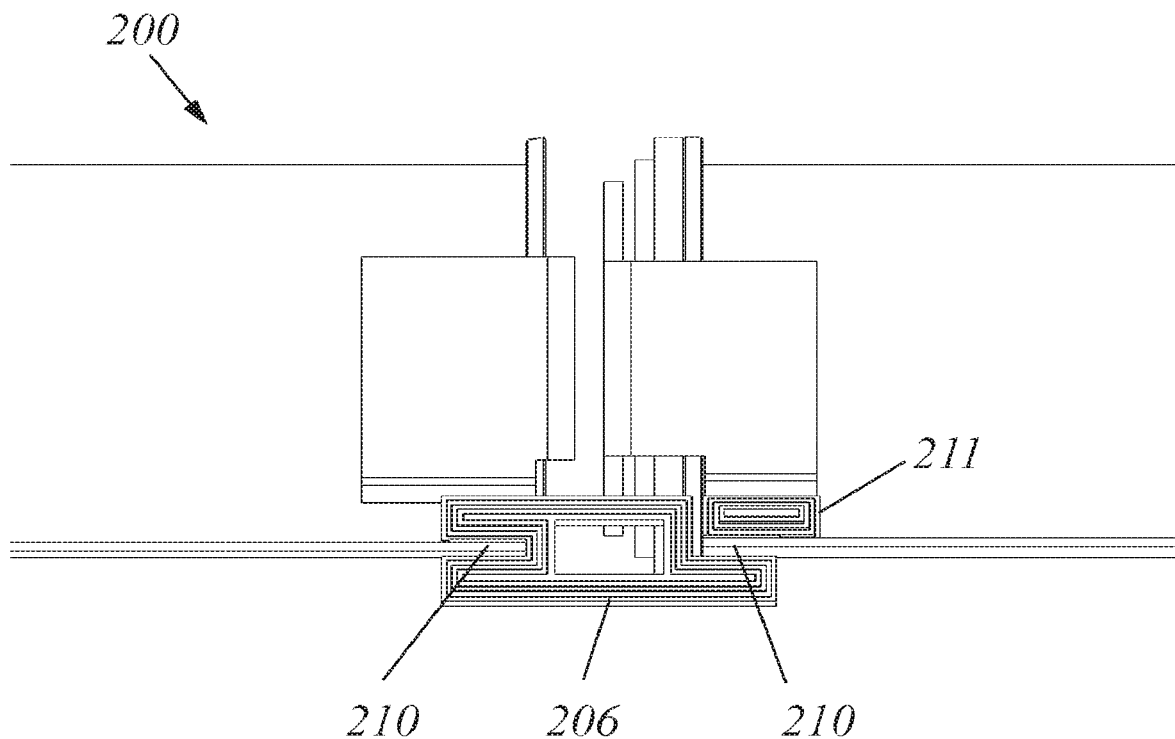

FIG. 10F shows radiation shield assembly 262 with a number of shielding segments 200 interconnected to form surrounding cover. Each pair of radiation shield segments (e.g., a first 200A and a second 200B radiation shield segments 200) are juxtapositionally arranged (horizontally or vertically, or in any angle). FIG. 10G shows one side of radiation shield assembly 262. As shown, each radiation shielding segment is fully individually controlled and can be deployed to a length independently of other radiation shielding segments, however the frame members of both sides of each radiation shield segment bridge across and cover any gap or seam through which unnecessary radiation can infiltrate through. In some embodiments, these frame members also contribute to the mechanical, functional and aesthetic behavior of the radiation protection apparatus, as they maintain the cover members substantially spread in both lateral (vertical) and horizontal axes, and themselves provide coverage in between adjacent cover members.

FIGS. 11A-11C schematically illustrate an exemplary radiation shield assembly 300 which includes a plurality of exemplary discrete radiation shield segments 301. Exemplary radiation shield assembly 300 may be part of a radiation protection apparatus, optionally, similar in function or/and structure to any of radiation protection apparatus 10, radiation protection apparatus 30, or radiation protection apparatus 260. Each radiation shield segment 301 includes a radiopaque cover member 302 arranged in a form of overlapping strips 303 (e.g., tiles). In some embodiments, radiopaque cover member 302 is substantially rigid, or alternatively, it may be substantially flexible so it can be bent or curved. An actuator 304 with scissors mechanism (pantograph) 305 is used for extending (FIG. 11C) or contracting (FIG. 11B) the cover member 302. A deployed length L of cover member 302 is determined according to extent of overlapping between each two adjacent strips 303, such that increasing overlapping will cause decreased deployed length and vice versa. This type of radiation shield segment may be assembled with extendable-contractible frame members such as previously described in order to provide lateral support to the strips 303 and in order to cover any gap or seam between adjacent shielding segments. Optionally, additionally or alternatively, scissors mechanism 305 functions or includes or is configured for connecting to one or more extendable-contractible frame member. Alternatively, a frame member may be formed as scissors mechanism while cover member 302 is deployed or withdrawn using other means such as a dispenser (e.g., dispenser 202 shown in FIG. 10E).

FIGS. 12A-12E schematically illustrate an exemplary (discrete), optionally, rigid, radiation shield segment 400 suitable for inclusion in any of the herein illustratively described exemplary embodiments of a radiation shield assembly, of any of the herein illustratively described exemplary embodiments of a radiation protection apparatus. In exemplary embodiments, the radiation protection apparatus may be similar in function or/and structure to any of exemplary radiation protection apparatus 10, exemplary radiation protection apparatus 30, or exemplary radiation protection apparatus 260, and may be similar in function or/and structure to exemplary radiation shield segments 100, or exemplary radiation shield segments 200, or exemplary radiation shield segments 301. The radiation shield segment 400 includes a first (single) frame member 401 formed of telescopically arranged frame sections 401$i$. In order to provide strength and structural support for entire radiation shield segment 400, frame member 401 may be formed of a high strength or/and a rigid material, while providing sufficient radiopacity due to high density characteristics. Such materials may include, as an example, tungsten, lead, or stainless steel alloys.

A singular frame member section 401$i$ is shown assembled in FIG. 12C and disassembled into main parts ('exploded view') in FIG. 12D. Each frame section 401$i$ includes two lateral flanges 403 connected with a wedge 404 from a first side, and connected at second side with both (lateral) ends of a section 405$i$ of a radiopaque cover member 405, provided in a form of tile (rigid, semi-rigid or flexible). Wedge 404 may optionally include a concavity 406 shaped to increase strength and structural stability to the frame section, and also accurately dimensioned to a minimal clearance and precise guiding for accurate engagement with other frame sections telescopically arranged therewith. Concavity 406 of each frame section 401$i$ may house an insert-plate 407 having a smooth surface, and optionally made of a stiff/rigid material, configured for reducing friction between moving surfaces of telescopically interconnected frames or/and for increasing strength and structural stability to the frame section.

In some embodiments, each radiopaque cover member section 405$i$ is substantially rigid, or alternatively, it may be substantially flexible so it can be bent or curved or rolled. An actuator 408 (in a form of a motor, with or without a drive train) is operatively connected with scissors mechanism (pantograph) 409 and together are applicable for extending or contracting the radiation shield segment 400 with cover member 405. A deployed length L of cover member 405 is determined according to extent of overlapping between each two adjacent sections (tiles) 405$i$, such that increasing overlapping will cause decreased deployed length and vice versa.

Flanges 403 are shaped with lateral extensions which are shaped and sized to cover any gap or seam between adjacent radiation shield segments of both sides thereof. Each flange 403 includes a protruding portion 410 and a recess portion 411, shaped and arranged such that protruding portion 410 can mate geometrically with recess portion 411, when laterally aligned and engaging therewith. FIG. 12E shows interconnection of a frame member section 401$a$ of a first shielding segment 400$a$ with an adjacent frame member section 401$b$ of a second shielding segment 400$b$ (similar to engagements/interconnections of radiation shield segments as shown, for example, in FIGS. 4, 9B, 10D, 10E and 11A). As shown, a protruding portion 410$a$ of first shielding segment 400$a$ mates geometrically with (e.g., nests in) a recess portion 411$b$ of second radiation shield segment 400$b$, in order to allow integration between adjacent discrete radiation shield segments while covering gaps or/and seams therebetween, using both frame members.

In some such embodiments (and as shown, for example, in FIG. 12E), when protruding portion 410$a$ completely or at least partially nests in recess portion 411$b$, it is also connected thereto with a connecting force, such as by use of magnetic or electromagnetic generated force field. For example, first frame member section 401$a$ includes a magnetizing element 412 and second frame member section 401$b$ includes a ferromagnetic element 413, whereby the magnetizing element may be a permanent magnet or an electromagnet, for example. Optionally, additionally or alternatively, magnetizing element 412 and a ferromagnetic element 413 may be formed or/and arranged as part of an electromagnetic brake system which may operate (connect/disconnect) automatically or selectively by a user.

FIGS. 13A-13B schematically illustrate an exemplary discrete radiation shield segment 500 operational with an exemplary push-strip (or push-wire) 503. Radiation shield segment 500 is shown as a singular manually operational model although it may be adapted to assemble with other similar radiation shield segments or/and be connected to an automatic/computerized control unit, drive mechanism, sensors, and the like, as previously described. Radiation shield segment 500 includes a first (single) frame member 501 including a plurality of telescopically arranged frame sections 501$i$, which may extend from a collapsed form (as shown in FIG. 13A) to an extended form (FIGS. 13B and 13C). Each frame section 501$i$ is stiff enough to maintain shape thereof, and provides sufficient opacity. A flexible radiopaque cover member 502 is configured to roll or unroll from a drum 504 into a chosen length, required/requested for shielding surrounding around periphery of a region of interest in an object.

A couple of push-strips 503 is coupled to or embedded in cover member 502, at both (lateral/rolled) sides thereof, as shown in FIG. 13C (which uncovers one push-strip 503 by illustratively clearing some frame sections 501$i$). The push-strips 503 are flexible enough in one axis, allowing it to roll with minimal resistance, together with cover member 502, but also are stiff enough and withstand substantial compression stress along its length. Hence, it can be pushed against a restraining (compressing) force while maintaining a straight form, unless it encounters a yielding force which may force it into collapsing. In some embodiments, a drive mechanism 505 in a form of a rotor (shown as a manually operational revolving handle, for illustrative purposes) is operatively coupled with one or both push strips 503 for actuating the entire radiation shield segment 500 into extension (by revolving the rotor in a first direction, thereby unrolling the push strips 503 with cover member 502) or contraction (by revolving the rotor in an opposite direction, thereby rolling the push strips 503 with cover member 502 back on drum 504). Push strips 503 may be formed of elastic strips of spring steel, relaxed in spiral (rolled) form.

In this exemplary embodiment, although not necessarily, the rigid frame members 501 are configured only to provide lateral or other rigidity to the entire shield member 500, allowing it to align in different elevation angles without compromise in structure or/and function, as previously described. A return spring 506 coupled to drum 504 may be used to assist or resist rotor 505 when extending (unrolling) radiation shield segment 500 thereby making it 'normally rolled' or 'normally unrolled' if needed.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to a single step, procedure, manner, means, or/and technique, or a sequence, set, or group of two or more steps, procedures, manners, means, or/and techniques, for accomplishing or achieving a given task or action. Any such herein disclosed method, in a non-limiting manner, may include one or more steps, procedures, manners, means, or/and techniques, that are known or readily developed from one or more steps, procedures, manners, means, or/and techniques, previously taught about by practitioners in the relevant field(s) and art(s) of the herein disclosed invention. In any such herein disclosed method, in a non-limiting manner, the stated or presented sequential order of one or more steps, procedures, manners, means, or/and techniques, is not limited to that specifically stated or presented sequential order, for accomplishing or achieving a given task or action, unless otherwise specifically defined or stated herein, or, unless the context clearly dictates otherwise. Accordingly, in any such herein disclosed method, in a non-limiting manner, there may exist one or more alternative sequential orders of the same steps, procedures, manners, means, or/and techniques, for accomplishing or achieving a same given task or action, while maintaining same or similar meaning and scope of the herein disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

The phrase 'operatively connected' (or 'operatively connectable'), as used herein, equivalently refers to the corresponding synonymous phrases 'operatively joined' (or 'operatively joinable'), and 'operatively attached' (or 'operatively attachable'), where the operative connection, operative joint, or operative attachment, is according to a physical, or/and electrical, or/and electronic, or/and mechanical, or/and electro-mechanical, manner or nature, involving various types and kinds of hardware or/and software equipment and components.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, are encompassed by the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A radiation protection apparatus for use with an X-ray system comprising a radiation source and a radiation detector having a beam axis therebetween, the radiation protection apparatus comprising:
    at least one radiation shield assembly including a support base operatively connectable to the radiation source or to the radiation detector of the X ray system, wherein the support base has a periphery at least partially surrounding the beam axis and a plurality of radiation shield segments attached laterally adjacent one another about at least a portion of the periphery of the support base, thereby forming a radiopaque screen disposed at least partially around a region of interest and together defining an edge configured to engage an object;
    wherein at least one of said plurality of radiation shield segments is individually controllable to extend or contract to a selected length to cause a respective free end thereof to move in a direction substantially parallel to the beam axis and away from or towards said support base, so as to change a contour of the edge of said radiopaque screen to conform to a surface curvature of the object engaged by said edge.

2. The radiation protection apparatus according to claim 1, further comprising:
    a control unit operatively connected to, and configured for actively controlling operation of, said at least one radiation shield assembly and said at least one of said radiation shield segments, thereby controlling movement of at least one of said free ends relative to an opposing portion of the object.

3. The radiation protection apparatus according to claim 2, wherein said control unit determines variable extensions of said radiation shield segments according to said selected length of said at least one of said radiation shield segments.

4. The radiation protection apparatus according to claim 2, further comprising:
    a drive mechanism, operatively connected to said radiation shield assembly and said control unit, and configured for extending or/and retracting a selected number of said radiation shield segments in accordance with said variable extensions determined by said control unit.

5. The radiation protection apparatus according to claim 4, wherein said drive mechanism includes a plurality of drivers and wherein each of said drivers is configured for extending or/and retracting a single separate unit or group of said radiation shield segments.

6. The radiation protection apparatus according to claim 4, wherein said drive mechanism is configured for globally extending or/and retracting all separate units or groups of said radiation shield segments.

7. The radiation protection apparatus according to claim 2, wherein said control unit determines said contour of said edge of the radiopaque screen edge correlatively with or/and in response to analysis of the surface curvature of the object.

8. The radiation protection apparatus according to claim 2, wherein said control unit includes a plurality of controllers, wherein each of said controllers is configured for controlling a single separate unit or group of said radiation shield segments.

9. The radiation protection apparatus according to claim 2, wherein said control unit is configured for globally controlling all separate units or groups of said radiation shield segments.

10. The radiation protection apparatus according to claim 1, wherein each of said radiation shield segments is individually extendable or retractable relative to said support base or/and relative to one or more others of said radiation shield segments in the direction substantially parallel to the beam axis.

11. The radiation protection apparatus according to claim 1, wherein each of said radiation shield segments is individually powered by a global power supply, or by a local power supply.

12. The radiation protection apparatus according to claim 11, wherein said global power supply is configured for globally providing power for operating all components of the radiation protection apparatus.

13. The radiation protection apparatus according to claim 11, wherein said local power supply is configured for locally providing power for operating a separate unit or group of said radiation shield segments.

14. The radiation protection apparatus according to claim 1, wherein each of said radiation shield segments is configured to be structurally rigid so as to retain a maximally extended shape along an extension axis that forms an elevation angle relative to direction of gravitational force acting upon said maximally extended shape.

15. The radiation protection apparatus according to claim 14, wherein said elevation angle is 15 degrees or more, optionally particularly 30 degrees or more, optionally particularly 45 degrees or more, optionally particularly 90 degrees or more.

16. The radiation protection apparatus according to claim 1, further comprising a sensing unit operatively connected to said at least one radiation shield assembly.

17. The radiation protection apparatus according to claim 16, wherein said sensing unit includes at least one positioning sensor coupled to at least one of said radiation shield segments and configured to sense and react to positioning or proximity of said at least one free end relative to said opposing portion of the object, or to a contact therebetween.

18. The radiation protection apparatus according to claim 16, wherein said sensing unit includes at least one radiation detecting sensor configured to detect a portion of the radiation emitted by said radiation source and leaking through said plurality of radiation shield segments.

19. The radiation protection apparatus according to claim 16, wherein said sensing unit is operatively connected to, and configured for providing data-information to, said control unit, whereby said control unit is responsive to said data-information provided by said sensing unit.

20. The radiation protection apparatus according to claim 1, wherein each of said radiation shield segments comprises a plurality of overlapping radiopaque tiles, wherein extending and retracting of said radiation shield segments respectively decreases and increases extent of overlap between said radiopaque tiles.

21. The radiation protection apparatus according to claim 1, wherein the edge configured to engage the object comprises a flexible spacer configured to move in at least one moving mode selected from the group consisting of bending, rotating, pivoting, compressing against the object, and conforming to a surface curvature of the object.

22. A radiation protection apparatus for shielding surroundings around the periphery of a region of interest located inside an object from radiation emitted by an X-ray system towards the object, the radiation protection apparatus comprising:
- at least one radiation shield assembly including a support base operatively connectable to a radiation source or a radiation detector of the X ray system and a plurality of radiation shield segments sequentially positioned relative to said support base, thereby forming a contiguous radiopaque screen configured for spanning at least partially around the region of interest periphery with an edge of said radiopaque screen opposing the object;
- wherein at least one of said radiation shield segments is individually controllable to extend or contract to a selected length with a respective free end thereof in a direction away from or towards said support base, so as to locally change contour of said radiopaque screen edge; and
- wherein at least one of said radiation shield segments includes:
- a radiopaque cover member ending with a cover member free end;
- a length dispenser operatively connected to said support base, said length dispenser is configured for covering a sector around said support base, and for controlling cover member length extending between said length dispenser and said cover member free end; and
- a first frame member operatively connected, via a first end thereof, to said length dispenser, and operatively connected, via a second end thereof, to said cover member free end, said first frame member is extendible or contractible according to control of said cover member length, and maintains structural rigidity sufficient for supporting said cover member in a laterally straight form along a chosen cover member deployed length.

23. The radiation protection apparatus according to claim 22, wherein said cover member is configured in a form of a roller-shade such that a remaining non-deployed length of said cover member is rolled inside of said dispenser.

24. The radiation protection apparatus according to claim 22, wherein said cover member is configured in a form of strips or tiles with selectively changeable overlapping, such that said cover member deployed length decreases by increasing overlapping between said strips or tiles.

25. The radiation protection apparatus according to claim 22, wherein said drive mechanism is configured to force said cover member or/and said first frame member to extend or contract when shifting from said chosen cover member deployed length.

26. The radiation protection apparatus according to claim 22, wherein said first frame member includes a plurality of first frame sections telescopically arranged and slidable inside one another or alongside one another.

27. The radiation protection apparatus according to claim 22, wherein said first frame member extends along said cover member deployed length, thereby covering a first side of said cover member.

28. The radiation protection apparatus according to claim 27, further comprising a second frame member extendible or contractible along said chosen cover member deployed length and above a second side of said cover member, opposing said first side thereof.

29. The radiation protection apparatus according to claim 28, wherein said first frame member is slidably interconnected with said adjacent second frame member.

30. The radiation protection apparatus according to claim 22, comprising a first and a second of said radiation shielding segments, juxtapositionally arranged, wherein said first radiation shielding segment is equipped with a first said cover member supported with said first frame member along a first adjacent side thereof, and said second radiation shielding segment is equipped with a second said cover member supported with said second frame member along a second adjacent side thereof, whereby said first radiation shielding segment adjacent side lies adjacent to said second radiation shielding segment adjacent side.

31. The radiation protection apparatus according to claim 30, wherein said first frame member includes a lateral extension sized for covering a gap spanning between said first radiation shielding segment adjacent side and said second radiation shielding segment adjacent side, or/and for covering said second radiation shielding segment adjacent side.

32. The radiation protection apparatus according to claim 31, wherein said second frame member is sized and shaped for mating against said lateral extension of said adjacent first frame member.

* * * * *